(12) United States Patent
Kapeller

(10) Patent No.: US 6,383,791 B1
(45) Date of Patent: May 7, 2002

(54) MOLECULES OF THE HKID-1-RELATED PROTEIN FAMILY AND USES THEREOF

(75) Inventor: Rosana Kapeller, Chestnut Hill, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/644,450

(22) Filed: Aug. 23, 2000

Related U.S. Application Data

(62) Division of application No. 09/237,543, filed on Jan. 26, 1999, now Pat. No. 6,143,540.

(51) Int. Cl.$^7$ ................................................. C12N 9/12
(52) U.S. Cl. ....................... 435/194; 435/183; 435/69.1; 435/91.1; 435/252.3; 435/320.1; 435/325; 435/15; 536/232

(58) Field of Search .................................. 435/194, 183, 435/69.1, 91.1, 252.3, 320.1, 325, 15; 536/23.2

Primary Examiner—Rebecca E. Prouty
Assistant Examiner—Richard Hutson
(74) Attorney, Agent, or Firm—Alston & Bird LLP

(57) ABSTRACT

Novel HKID-1 polypeptides, proteins, and nucleic acid molecules are disclosed. In addition to isolated, full-length HKID-1 proteins, the invention further provides isolated HKID-1 fusion proteins, antigenic peptides and anti-HKID-1 antibodies. The invention also provides HKID-1 nucleic acid molecules, recombinant expression vectors containing a nucleic acid molecule of the invention, host cells into which the expression vectors have been introduced and non-human transgenic animals in which an HKID-1 gene has been introduced or disrupted. Diagnostic, screening and therapeutic methods utilizing compositions of the invention are also provided.

5 Claims, 5 Drawing Sheets

SEQ ID NO:1
GGCGCTCCGCCTGCTGCGCGTCTACGCGGTCCCCGCGGGCCTTCCGGGCCCACTGCGCCG
CGCGGACCGCCTCGGGCTCGGACGGCCGGTGTCCCCGGCGCGCCGCTCGCCCGGATCGGC
CGCGGCTTCGGCGCCTGGGGCTCGGGGCTCCGGGGAGGCCGTCGCCCGCGATGCTGCTCT
CCAAGTTCGGCTCCCTGGCGCACCTCTGCGGGCCCGGCGGCGTGGACCACCTCCCGGTGA
AGATCCTGCAGCCAGCCAAGGCGGACAAGGAGAGCTTCGAGAAGGCGTACCAGGTGGGCG
CCGTGCTGGGTAGCGGCGGCTTCGGCACGGTCTACGCGGGTAGCCGCATCGCCGACGGGC
TCCCGGTGGCTGTGAAGCACGTGGTGAAGGAGCGGGTGACCGAGTGGGGCAGCCTGGGCG
GCGCGACCGTGCCCCTGGAGGTGGTGCTGCTGCGCAAGGTGGGCGCGGCGGGCGGCGCGC
GCGGCGTCATCCGCCTGCTGGACTGGTTCGAGCGGCCCGACGGCTTCCTGCTGGTGCTGG
AGCGGCCCGAGCCGGCGCAGGACCTCTTCGACTTTATCACGGAGCGCGGCGCCCTGGACG
AGCCGCTGGCGCGCCGCTTCTTCGCGCAGGTGCTGGCCGCCGTGCGCCACTGCCACAGCT
GCGGGGTCGTGCACCGCGACATTAAGGACGAAAATCTGCTTGTGGACCTGCGCTCCGGAG
AGCTCAAGCTCATCGACTTCGGTTCGGGTGCGCTGCTCAAGGACACGGTCTACACCGACT
TCGACGGCACCCGAGTGTACAGCCCCCCGGAGTGGATCCGCTACCACCGCTACCACGGGC
GCTCGGCCACCGTGTGGTCGCTGGGCGTGCTTCTCTACGATATGGTGTGTGGGGACATCC
CCTTCGAGCAGGACGAGGAGATCCTCCGAGGCCGCCTGCTCTTCCGGAGGAGGGTCTCTC
CAGAGTGCCAGCAGCTGATCCGGTGGTGCCTGTCCCTGCGGCCCTCAGAGCGGCCGTCGC
TGGATCAGATTGCGGCCCATCCCTGGATGCTGGGGGCTGACGGGGGCGCCCCGGAGAGCT
GTGACCTGCGGCTGTGCACCCTCGACCCTGATGACGTGGCCAGCACCACGTCCAGCAGCG
AGAGCTTGTGAGGAGCTGCACCTGACTGGGAGCTAGGGGACCACCTGCCTTGGCCAGACC
TGGGACGCCCCAGACCCTGACTTTTTCCTGCGTGGGCCGTCTCCTCCTGCGGAAGCAGT
GACCTCTGACCCCTGGTGACCTTCGCTTTGAGTGCCTTTTGAACGCTGGTCCCGCGGGAC
TTGGTTTTCTCAAGCTCTGTCTGTCCAAAGACGCTCCGGTCGAGGTCCCGCCTGCCCTGG
GTGGATACTTGAACCCCAGACGCCCCTCTGTGCTGCTGTGTCCGGAGGCGGCCTTCCCAT
CTGCCTGCCCACCCGGAGCTCTTTCCGCCGGCGCAGGGTCCCAAGCCCACCTCCCGCCCT
CAGTCCTGCGGTGTGCGTCTGGGCACGTCCTGCACACACAATGCAAGTCCTGGCYTCCGC
GCCCGCCCGCCCACGCGAGCCGTACCCGCCGCCAACTCTGTTATTTATGGTGTGACCCCC
TGGAGGTGCCCTCGGCCCACCGGGGCTATTTATTGTTTAATTTATTTGTTGAGGTTATTT
CCTCTGAGCAGTCTGCCTCTCCCAAGCCCCAGGGGACAGTGGGGAGGCAGGGGAGGGGGT
GGCTGTGGTCCAGGGACCCCAGGCCCTGATTCCTGTGCCTGGCGTCTGTCCTGGCCCCGC
CTGTCAGAAGATGAACATGTATAGTGGCTAACTTAAGGGGAGTGGGTGACCCTGACACTT
CCAGGCACTGTGCCCAGGGTTTGGGTTTTAAATTATTGACTTTGTACAGTCTGCTTGTGG
GCTCTGAAAGCTGGGGTGGGGCCAGAGCCTGAGCGTTTAATTTATTCAGTACCTGTGTTT
GTGTGAATGCGGTGTGTGCAGGCATCGCAGATGGGGGTTCTTTCAGTTCAAAAGTGAGAT
GTCTGGAGATCATATTTTTTTATACAGGTATTTCAATTAAAATGTTTTGTACATAGAAA
AAAAAAAAAAAAAAAAAAAGGGCGG
SEQ ID NO:2
MLLSKFGSLAHLCGPGGVDHLPVKILQPAKADKESFEKAYQVGAVLGSGGFGTVYAGSRIADGLP
VAVKHVVKERVTEWGSLGGATVPLEVVLLRKVGAAGGARGVIRLLDWFERPDGFLLVLERPEPAQ
DLFDFITERGALDEPLARRFFAQVLAAVRHCHSCGVVHRDIKDENLLVDLRSGELKLIDFGSGAL
LKDTVYTDFDGTRVYSPPEWIRYHRYHGRSATVWSLGVLLYDMVCGDIPFEQDEEILRGRLLFRR

Figure 1A

RVSPECQQLIRWCLSLRPSERPSLDQIAAHPWMLGADGGAPESCDLRLCTLDPDDVASTTSSSES
L

SEQ ID NO:3

ATGCTGCTCTCCAAGTTCGGCTCCCTGGCGCACCTCTGCGGGCCCGGCGGCGTGGACCACCTCCC
GGTGAAGATCCTGCAGCCAGCCAAGGCGGACAAGGAGAGCTTCGAGAAGGCGTACCAGGTGGGCG
CCGTGCTGGGTAGCGGCGGCTTCGGCACGGTCTACGCGGGTAGCCGCATCGCCGACGGGCTCCCG
GTGGCTGTGAAGCACGTGGTGAAGGAGCGGGTGACCGAGTGGGGCAGCCTGGGCGGCGCGACCGT
GCCCCTGGAGGTGGTGCTGCTGCGCAAGGTGGGCGCGGCGGGCGGCGCGCGGCGTCATCCGCC
TGCTGGACTGGTTCGAGCGGCCCGACGGCTTCCTGCTGGTGCTGGAGCGGCCCGAGCCGGCGCAG
GACCTCTTCGACTTTATCACGGAGCGCGGCGCCCTGGACGAGCCGCTGGCGCGCCGCTTCTTCGC
GCAGGTGCTGGCCGCCGTGCGCCACTGCCACAGCTGCGGGGTCGTGCACCGCGACATTAAGGACG
AAAATCTGCTTGTGGACCTGCGCTCCGGAGAGCTCAAGCTCATCGACTTCGGTTCGGGTGCGCTG
CTCAAGGACACGGTCTACACCGACTTCGACGGCACCCGAGTGTACAGCCCCCCGGAGTGGATCCG
CTACCACCGCTACCACGGGCGCTCGGCCACCGTGTGGTCGCTGGGCGTGCTTCTCTACGATATGG
TGTGTGGGGACATCCCCTTCGAGCAGGACGAGGAGATCCTCCGAGGCCGCCTGCTCTTCCGGAGG
AGGGTCTCTCCAGAGTGCCAGCAGCTGATCCGGTGGTGCCTGTCCCTGCGGCCCTCAGAGCGGCC
GTCGCTGGATCAGATTGCGGCCCATCCCTGGATGCTGGGGGCTGACGGGGGCGCCCCGGAGAGCT
GTGACCTGCGGCTGTGCACCCTCGACCCTGATGACGTGGCCAGCACCACGTCCAGCAGCGAGAGC
TTG

Figure 1B

```
                                                          Score   E-value
                                                          -----   -------
        PF00069 Eukaryotic protein kinase domain          262.4   5.9e-75 yelleklGeGsfGkVykakhk.tgkivAvKilkkesls.........
              y+++ +lG+G+fG+Vy + ++ +g +vAvK + ke++ + ++ ++
           40 YQVGAVLGSSGGFGTVYAGSRIaDGLPVAVKHVVKERVTewgslggat 86

.lrEiqilkrls....HpNIvrllgvfedtddhlylvmEymegG.dLfdy
                E+ +l+++    ++    ++rll++fe ++d + lv+E   e  +dLfd+
           87 vPLEVVLLRKVGaaggARGVIRLLDWFE-RPDGFLLVLERPEPAqDLFDF 135 lrrngplsekeakkialQilrGleYLHsngivHRDLKpeNILlden.gtv
              ++++g+l+e+ a++++ Q+l ++  ++Hs+g+vHRD+K eN+L+d ++g +
          136 ITERGALDEPLARRFFAQVLAAVRHCHSCGVVHRDIKDENLLVDLRsGEL 185

KiaDFGLArll..eklttfvGTpwYmmAPEvileg.rgysskvDvWSlGv
              K++DFG  +ll+++++++t+f GT++Y   +PE+ ++++r++++ + vWSlGv
          186 KLIDFGSGALLkdTVYTDFDGTRVYS-PPEW-IRYhRYHGRSATVWSLGV 233 iLyElltggplfpgadlpaftggdevdqliifvlklPfsdelpktridpl
              +Ly +++g                             ++Pf++
          234 LLYDMVCG------------------------DIPFEQ---------D 248 eelfrikkrrlplpsncSeelkdLlkkcLnkDPskRpGsatakeilnhpw
              ee++r+ +      + +++S+e+++L+++cL + Ps+Rp    +  +i +hpw
          249 EEILRGRLL---FRRRVSPECQQLIRWCLSLRPSERP---SLDQIAAHPW 292 f
                +
          293   M   293                    Figure 2
```

```
       MLLSKIGSLAHLCRAGPCNDLHAKILAPGK-DKEPLESQY Majority
                10        20        30        40
     1 MLLSKFGSLAHICNPSNMEHLPVKILQPVKVDKEPFEKVY frog_PIM-1.PRO
     1 MLLSKFGSLAHLCGPGGVDHLPVKILQPAKADKESFEKAY HKID-1.pro
     1 MLLSKINSLAHL-RAAPCNDLHATKLAPGK-EKEPLESQY human_PIM-1.PRO
     1 MLLSKINSLAHL-RARPCNDLHATKLAPGK-EKEPLESQY murine_PIM-1.PRO
     1 MLLSKFGSLAHLCGPGGVDHLPVKILQPAKADKESFEKVY rat_KID-1.pro
     1 MLLSKINSLAHL-RAAPCNDLHANKLAPGK-EKEPLESQY rat_PIM-1.PRO QVGPVLGSGGFGSVYSGIRVADGLPVAVKHVEKDRVSDWG Majority
                50        60        70        80
    41 QVGSVVASGGFGTVYSDSRIADGQPVAVKHVAKERVTEWG frog_PIM-1.PRO
    41 QVGAVLGSGGFGTVYAGSRIADGLPVAVKHVVKERVTEWG HKID-1.pro
    39 QVGPLLGSGGFGSVYSGIRVSDNLPVAIKHVEKDRISDWG human_PIM-1.PRO
    39 QVGPLLGSGGFGSVYSGIRVADNLPVAIKHVEKDRISDWG murine_PIM-1.PRO
    41 QVGAVLGSGGFGTVYAGSRIADGLPVAVKHVVKERVTEWG rat_KID-1.pro
    39 QVGPLLGSGGFGSVYSGIRVADNLPVAIKHVEKDRISDWG rat_PIM-1.PRO ELPNGTRVPLEVVLLKKVSSA--FSGVIRLLDWFERPDSF Majority
                90       100       110       120
    81 TL-NGVMVPLEIVLLKKVPTA--FRGVINLLDWYERPDAF frog_PIM-1.PRO
    81 SL-GGATVPLEVVLLRKVGAAGGARGVIRLLDWFERPDGF HKID-1.pro
    79 ELPNGTRVPMEVVLLKKVSSG--FSGVIRLLDWFERPDSF human_PIM-1.PRO
    79 ELPNGTRVPMEVVLLKKVSSD--FSGVIRLLDWFERPDSF murine_PIM-1.PRO
    81 SL-GGMAVPLEVVLLRKVGAAGGARGVIRLLDWFERPDGF rat_KID-1.pro
    79 ELPNGTRVPMEVVLLKKVSSG--FSGVIRLLDWFERPDSF rat_PIM-1.PRO VLVLERPEPVQDLFDFITERGALDEDLARGFFWQVLEAVR Majority
               130       140       150       160
   118 LIVMERPEPVKDLFDYITEKGPLDEDTARGFFRQVLEAVR frog_PIM-1.PRO
   120 LLVLERPEPAQDLFDFITERGALDEPLARRFFAQVLAAVR HKID-1.pro
   117 VLILERPEPVQDLFDFITERGALQEELARSFFWQVLEAVR human_PIM-1.PRO
   117 VLVLERPEPVQDLFDFITERGALQEELARGFFWQVLEAVR murine_PIM-1.PRO
   120 LLVLERPEPAQDLFDFITERGALDEPLARRFFAQVLAAVR rat_KID-1.pro
   117 VLILERPEPVQDLFDFITERGALQEELARSFFWQVLEAVR rat_PIM-1.PRO HCHNCGVVHRDIKDENLLVDLRRGELKLIDFGSGALLKDT Majority
               170       180       190       200
   158 HCYNCGVVHRDIKDENLLVDTRNGELKLIDFGSGALLKDT frog_PIM-1.PRO
   160 HCHSCGVVHRDIKDENLLVDTRSGELKLIDFGSGALLKDT HKID-1.pro
   157 HCHNCGVLHRDIKDENLLIDLNRGELKLIDFGSGALLKDT human_PIM-1.PRO
   157 HCHNCGVLHRDIKDENILIDLSRGEIKLIDFGSGALLKDT murine_PIM-1.PRO
   160 HCHNCGVLHRDIKDENLLVDLRSGELKLIDFGSGAVLKDT rat_KID-1.pro
   157 HCHNCGVLHRDIKDENILIDLNRGELKLIDFGSGALLKDT rat_PIM-1.PRO VYTDFDGTRVYSPPEWIRYHRYHGRSAAVWSLGVLLYDMV Majority
               210       220       230       240
   198 VYTDFDGTRVYSPPEWVRYHRYHGRSATVWSLGVLLYDMV frog_PIM-1.PRO
   200 VYTDFDGTRVYSPPEWIRYHRYHGRSATVWSLGVLLYDMV HKID-1.pro
   197 VYTDFDGTRVYSPPEWIRYHRYHGRSAAVWSLGILLYDMV human_PIM-1.PRO
   197 VYTDFDGTRVYSPPEWIRYHRYHGRSAAVWSLGVLLYDMV murine_PIM-1.PRO
   200 VYTDFDGTRVYSPPEWIRYHRYHGRSATVWSLGVLLYDMV rat_KID-1.pro
   197 VYTDFDGTRVYSPPEWIRYHRYHGRSAAVWSLGILLYDMV rat_PIM-1.PRO CGDIPFEQDEEIVRGQVFFRQRVSSECQQLIRWCLSLRPS Majority
               250       260       270       280
   238 YGDIPFEQDEEIVRVRLCFRRRISTECQQLIKWCLSLRPS frog_PIM-1.PRO
   240 CGDIPFEQDEEILRGRLLFRRRVSPECQQLIRWCLSLRPS HKID-1.pro
   237 CGDIPFEHDEEIIRGQVFFRQTVSSECQHLIRWCLALRPS human_PIM-1.PRO
   237 CGDIPFEQDEEIVRGQVFFRQRVSSECQHLIRWCLSLRPS murine_PIM-1.PRO
   240 CGDIPFEQDEEILRGRLFFRRRVSPECQQLIEWCLSLRPS rat_KID-1.pro
   237 CGDIPFEHDEEIVKGQVYFRQRVSSECQHLIRWCLSLRPS rat_PIM-1.PRO DRPSLEEIANHPWM-QDDLLPQETCDLHLHSLS-PDSSST Majority
               290       300       310       320
   278 DRPTLEQIFDHPWMCKCDLVKSEDCDLRLRTID-NDSSST frog_PIM-1.PRO
   280 ERPSLDQIAAHPWMLGADGGAPESCDLRLCTLDPDDVAST HKID-1.pro
   277 DRPTFEEIQNHPWM-QDVLLPQETAEIHLHSLS-PGPSK  human_PIM-1.PRO
   277 DRPSFEEIRNHPWM-QGDLLPQAASEIHLHSLS-PGSSK  murine_PIM-1.PRO
   280 ERPSLDQIAAHPWMLGTEGSVPENCDLRLCALDTDDGAST rat_KID-1.pro
   277 DRPSFEEIQNHPWM-QDVLLPQATAEIHLHSLS-PSPSK  rat_PIM-1.PRO -SS-ESL                                 Majority 317 SSSNESL                                 frog_PIM-1.PRO
   320 TSSSESL                                 HKID-1.pro
   313                                         human_PIM-1.PRO
   313                                         murine_PIM-1.PRO
   320 TSSSESL                                 rat_KID-1.pro
   313                                         rat_PIM-1.PRO
```

Figure 4

SEQUENCE LISTING

<160> NUMBER OF SEQ ID NOS: 11

<210> SEQ ID NO 1
<211> LENGTH: 2126
<212> TYPE: DNA
<213> ORGANISM: Homo sapiens

<400> SEQUENCE: 1

```
ggcgctccgc ctgctgcgcg tctacgcggt ccccgcgggc cttccgggcc cactgcgccg      60
cgcggaccgc ctcgggctcg gacggccggt gtccccggcg cgccgctcgc ccggatcggc     120
cgcggcttcg gcgcctgggg ctcggggctc cggggaggcc gtcgcccgcg atgctgctct     180
ccaagttcgg ctccctggcg cacctctgcg ggcccggcgg cgtggaccac ctcccggtga     240
agatcctgca gccagccaag gcggacaagg agagcttcga gaaggcgtac caggtgggcg     300
ccgtgctggg tagcggcggc ttcggcacgg tctacgcggg tagccgcatc gccgacgggc     360
tcccggtggc tgtgaagcac gtggtgaagg agcgggtgac cgagtggggc agcctgggcg     420
```

-continued

```
gcgcgaccgt gccgctggag gtggtgctgc tgcgcaaggt gggcgcggcg ggcggcgcgc      480
gcggcgtcat ccgcctgctg gactggttcg agcggcccga cggcttcctg ctggtgctgg      540
agcggcccga gccggcgcag gacctcttcg actttatcac ggagcgcggc gccctggacg      600
agccgctggc gcgccgcttc ttcgcgcagg tgctggccgc cgtgcgccac tgccacagct      660
gcggggtcgt gcaccgcgac attaaggacg aaaatctgct tgtggacctg cgctccggag      720
agctcaagct catcgacttc ggttcgggtg cgctgctcaa ggacacggtc tacaccgact      780
tcgacggcac ccgagtgtac agccccccgg agtggatccg ctaccaccgc taccacgggc      840
gctcggccac cgtgtggtcg ctgggcgtgc ttctctacga tatggtgtgt ggggacatcc      900
ccttcgagca ggacgaggag atcctccgag gccgcctgct cttccggagg agggtctctc      960
cagagtgcca gcagctgatc cggtggtgcc tgtccctgcg cccctcagag cggccgtcgc     1020
tggatcagat gcggcccat ccctggatgc tgggggctga cggggcgcc ccggagagct     1080
gtgacctgcg gctgtgcacc ctcgaccctg atgacgtggc cagcaccacg tccagcagcg     1140
agagcttgtg aggagctgca cctgactggg agctagggga ccacctgcct ggccagacc     1200
tgggacgccc ccagaccctg acttttttcct gcgtgggccg tctcctcctg cggaagcagt     1260
gacctctgac ccctggtgac cttcgctttg agtgccttttt gaacgctggt cccgcgggac     1320
ttggttttct caagctctgt ctgtccaaag acgctccggt cgaggtcccg cctgccctgg     1380
gtggatactt gaaccccaga cgcccctctg tgctgctgtg tccggaggcg gccttcccat     1440
ctgcctgccc accggagct ctttccgccg cgcagggtc ccaagcccac ctcccgcccct     1500
cagtcctgcg gtgtgcgtct gggcacgtcc tgcacacaca atgcaagtcc tggcytccgc     1560
gcccgcccgc ccacgcgagc cgtacccgcc gccaactctg ttatttatgg tgtgaccccc     1620
tggaggtgcc ctcggcccac cggggctatt tattgtttaa tttatttgtt gaggttattt     1680
cctctgagca gtctgcctct cccaagcccc aggggacagt ggggaggcag gggagggggt     1740
ggctgtggtc cagggacccc aggccctgat tcctgtgcct ggcgtctgtc ctggccccgc     1800
ctgtcagaag atgaacatgt atagtggcta acttaagggg agtgggtgac cctgacactt     1860
ccaggcactg tgcccagggt ttgggtttta aattattgac tttgtacagt ctgcttgtgg     1920
gctctgaaag ctggggtggg gccagagcct gagcgtttaa tttattcagt acctgtgttt     1980
gtgtgaatgc ggtgtgtgca ggcatcgcag atgggggttc tttcagttca aaagtgagat     2040
gtctggagat catatttttt tatacaggta tttcaattaa aatgttttg tacatagaaa     2100
aaaaaaaaaa aaaaaaaaa gggcgg                                          2126
```

<210> SEQ ID NO 2
<211> LENGTH: 326
<212> TYPE: PRT
<213> ORGANISM: Homo sapiens

<400> SEQUENCE: 2

Met Leu Leu Ser Lys Phe Gly Ser Leu Ala His Leu Cys Gly Pro Gly
 1               5                  10                  15

Gly Val Asp His Leu Pro Val Lys Ile Leu Gln Pro Ala Lys Ala Asp
                20                  25                  30

Lys Glu Ser Phe Glu Lys Ala Tyr Gln Val Gly Ala Val Leu Gly Ser
            35                  40                  45

Gly Gly Phe Gly Thr Val Tyr Ala Gly Ser Arg Ile Ala Asp Gly Leu
        50                  55                  60

Pro Val Ala Val Lys His Val Val Lys Glu Arg Val Thr Glu Trp Gly

|     |     |     |     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- | --- | --- | --- |
Ser Leu Gly Gly Ala Thr Val Pro Leu Glu Val Val Leu Leu Arg Lys
            85                  90                  95

Val Gly Ala Ala Gly Gly Ala Arg Gly Val Ile Arg Leu Leu Asp Trp
            100                 105                 110

Phe Glu Arg Pro Asp Gly Phe Leu Leu Val Leu Glu Arg Pro Glu Pro
            115                 120                 125

Ala Gln Asp Leu Phe Asp Phe Ile Thr Glu Arg Gly Ala Leu Asp Glu
            130                 135                 140

Pro Leu Ala Arg Arg Phe Ala Gln Val Leu Ala Ala Val Arg His
145                 150                 155                 160

Cys His Ser Cys Gly Val Val His Arg Asp Ile Lys Asp Glu Asn Leu
            165                 170                 175

Leu Val Asp Leu Arg Ser Gly Glu Leu Lys Leu Ile Asp Phe Gly Ser
            180                 185                 190

Gly Ala Leu Leu Lys Asp Thr Val Tyr Thr Asp Phe Asp Gly Thr Arg
            195                 200                 205

Val Tyr Ser Pro Pro Glu Trp Ile Arg Tyr His Arg Tyr His Gly Arg
    210                 215                 220

Ser Ala Thr Val Trp Ser Leu Gly Val Leu Leu Tyr Asp Met Val Cys
225                 230                 235                 240

Gly Asp Ile Pro Phe Glu Gln Asp Glu Glu Ile Leu Arg Gly Arg Leu
            245                 250                 255

Leu Phe Arg Arg Arg Val Ser Pro Glu Cys Gln Gln Leu Ile Arg Trp
            260                 265                 270

Cys Leu Ser Leu Arg Pro Ser Glu Arg Pro Ser Leu Asp Gln Ile Ala
            275                 280                 285

Ala His Pro Trp Met Leu Gly Ala Asp Gly Gly Ala Pro Glu Ser Cys
            290                 295                 300

Asp Leu Arg Leu Cys Thr Leu Asp Pro Asp Asp Val Ala Ser Thr Thr
305                 310                 315                 320

Ser Ser Ser Glu Ser Leu
            325

<210> SEQ ID NO 3
<211> LENGTH: 978
<212> TYPE: DNA
<213> ORGANISM: Homo sapiens

<400> SEQUENCE: 3
atgctgctct ccaagttcgg ctccctggcg cacctctgcg ggcccggcgg cgtggaccac     60
ctcccggtga agatcctgca gccagccaag gcggacaagg agagcttcga aaggcgtac    120 caggtgggcg ccgtgctggg tagcggcggc ttcggcacgg tctacgcggg tagccgcatc    180
gccgacgggc tcccggtggc tgtgaagcac gtggtgaagg agcgggtgac cgagtggggc    240
agcctgggcg gcgcgaccgt gcccctggag gtggtgctgc tgcgcaaggt gggcgcggcg    300
ggcggcgcgc gcggcgtcat ccgcctgctg gactggttcg agcggcccga cggcttcctg    360
ctggtgctgg agcggcccga gccggcgcag gacctcttcg actttatcac ggagcgcggc    420
gccctggacg agccgctggc gcgccgcttc ttcgcgcagg tgctggccgc cgtgcgccac    480
tgccacagct gcggggtcgt gcaccgcgac attaaggacg aaaatctgct tgtggacctg    540
cgctccggag agctcaagct catcgacttc ggttcgggtg cgctgctcaa ggacacggtc    600
tacaccgact cgacggcac ccgagtgtac agcccccgg agtggatccg ctaccaccgc    660

-continued

```
taccacgggc gctcggccac cgtgtggtcg ctgggcgtgc ttctctacga tatggtgtgt    720
ggggacatcc ccttcgagca ggacgaggag atcctccgag ccgcctgct cttccggagg     780 agggtctctc cagagtgcca gcagctgatc cggtggtgcc tgtccctgcg gccctcagag    840
cggccgtcgc tggatcagat tgcggcccat ccctggatgc tgggggctga cgggggcgcc    900
ccggagagct gtgacctgcg gctgtgcacc ctcgaccctg atgacgtggc cagcaccacg    960
tccagcagcg agagcttg                                                  978
```

<210> SEQ ID NO 4
<211> LENGTH: 254
<212> TYPE: PRT
<213> ORGANISM: Artificial Sequence
<220> FEATURE:
<223> OTHER INFORMATION: Description of Artificial Sequence: eukaryotic
      protein kinase domain

<400> SEQUENCE: 4

Tyr Gln Val Gly Ala Val Leu Gly Ser Gly Gly Phe Gly Thr Val Tyr
 1               5                  10                  15

Ala Gly Ser Arg Ile Ala Asp Gly Leu Pro Val Ala Val Lys His Val
            20                  25                  30

Val Lys Glu Arg Val Thr Glu Trp Gly Ser Leu Gly Gly Ala Thr Val
        35                  40                  45

Pro Leu Glu Val Val Leu Arg Lys Val Gly Ala Ala Gly Gly Ala
    50                  55                  60

Arg Gly Val Ile Arg Leu Leu Asp Trp Phe Glu Arg Pro Asp Gly Phe
65                  70                  75                  80

Leu Leu Val Leu Glu Arg Pro Glu Pro Ala Gln Asp Leu Phe Asp Phe
                85                  90                  95

Ile Thr Glu Arg Gly Ala Leu Asp Glu Pro Leu Ala Arg Arg Phe Phe
            100                 105                 110

Ala Gln Val Leu Ala Ala Val Arg His Cys His Ser Cys Gly Val Val
        115                 120                 125

His Arg Asp Ile Lys Asp Glu Asn Leu Leu Val Asp Leu Arg Ser Gly
    130                 135                 140

Glu Leu Lys Leu Ile Asp Phe Gly Ser Gly Ala Leu Leu Lys Asp Thr
145                 150                 155                 160

Val Tyr Thr Asp Phe Asp Gly Thr Arg Val Tyr Ser Pro Pro Glu Trp
                165                 170                 175

Ile Arg Tyr His Arg Tyr His Gly Arg Ser Ala Thr Val Trp Ser Leu
            180                 185                 190

Gly Val Leu Leu Tyr Asp Met Val Cys Gly Asp Ile Pro Phe Glu Gln
        195                 200                 205

Asp Glu Glu Ile Leu Arg Gly Arg Leu Leu Phe Arg Arg Val Ser
    210                 215                 220

Pro Glu Cys Gln Gln Leu Ile Arg Trp Cys Leu Ser Leu Arg Pro Ser
225                 230                 235                 240

Glu Arg Pro Ser Leu Asp Gln Ile Ala Ala His Pro Trp Met
                245                 250

<210> SEQ ID NO 5
<211> LENGTH: 455
<212> TYPE: PRT
<213> ORGANISM: Rattus norvegicus

<400> SEQUENCE: 5

```
Met Pro Lys Leu His Gln Pro Leu Val Asn Arg Gln Gly Ala Ser Gly
 1               5                  10                  15

Phe Pro Ser Thr Thr Leu Pro Asp Ser Lys Gln Pro His Arg Lys Val
                20                  25                  30

Ser Leu Gly Arg Lys Glu Ala Glu Leu Gln Ala Ala Pro Pro Pro Arg
            35                  40                  45

Arg Asp Thr Cys Leu Arg Gly Pro Lys Pro Arg Gly Glu Ala Ala Gly
        50                  55                  60

Ala Cys Glu Pro Leu Gly Gln Leu Pro Ser Thr Gly Phe Arg Ala Ala
 65                  70                  75                  80

Thr Gly Gln Leu Arg Arg Ala Ala Pro Leu Ser Ala Arg Pro Arg
                85                  90                  95

Gly Arg Gly Ile Arg Arg Ala Val Cys Gly Gln Glu Asp Arg Pro Pro
                100                 105                 110

Ala Ser Val Pro Asp Gly Ser Glu Ala Ala Pro His Ala Arg Pro Pro
            115                 120                 125

Ala Met Leu Leu Ser Lys Phe Gly Ser Leu Ala His Leu Cys Gly Pro
    130                 135                 140

Gly Gly Val Asp His Leu Pro Val Lys Ile Leu Gln Pro Ala Lys Ala
145                 150                 155                 160

Asp Lys Glu Ser Phe Glu Lys Val Tyr Gln Val Gly Ala Val Leu Gly
                165                 170                 175

Ser Gly Gly Phe Gly Thr Val Tyr Ala Gly Ser Arg Ile Ala Asp Gly
            180                 185                 190

Leu Pro Val Ala Val Lys His Val Val Lys Glu Arg Val Thr Glu Trp
        195                 200                 205

Gly Ser Leu Gly Gly Met Ala Val Pro Leu Glu Val Val Leu Leu Arg
    210                 215                 220

Lys Val Gly Ala Ala Gly Ala Arg Gly Val Ile Arg Leu Leu Asp
225                 230                 235                 240

Trp Phe Glu Arg Pro Asp Gly Phe Leu Leu Val Leu Glu Arg Pro Glu
                245                 250                 255

Pro Ala Gln Asp Leu Phe Asp Phe Ile Thr Glu Arg Gly Ala Leu Asp
            260                 265                 270

Glu Pro Leu Ala Arg Arg Phe Phe Ala Gln Val Leu Ala Ala Val Arg
        275                 280                 285

His Cys His Asn Cys Gly Val Val His Arg Asp Ile Lys Asp Glu Asn
    290                 295                 300

Leu Leu Val Asp Leu Arg Ser Gly Glu Leu Lys Leu Ile Asp Phe Gly
305                 310                 315                 320

Ser Gly Ala Val Leu Lys Asp Thr Val Tyr Thr Asp Phe Asp Gly Thr
                325                 330                 335

Arg Val Tyr Ser Pro Pro Glu Trp Ile Arg Tyr His Arg Tyr His Gly
            340                 345                 350

Arg Ser Ala Thr Val Trp Ser Leu Gly Val Leu Leu Tyr Asp Met Val
        355                 360                 365

Cys Gly Asp Ile Pro Phe Glu Gln Asp Glu Glu Ile Leu Arg Gly Arg
    370                 375                 380

Leu Phe Phe Arg Arg Arg Val Ser Pro Glu Cys Gln Gln Leu Ile Glu
385                 390                 395                 400

Trp Cys Leu Ser Leu Arg Pro Ser Glu Arg Pro Ser Leu Asp Gln Ile
                405                 410                 415
```

Ala Ala His Pro Trp Met Leu Gly Thr Glu Gly Ser Val Pro Glu Asn
            420                 425                 430

Cys Asp Leu Arg Leu Cys Ala Leu Asp Thr Asp Asp Gly Ala Ser Thr
            435                 440                 445

Thr Ser Ser Ser Glu Ser Leu
            450                 455

<210> SEQ ID NO 6
<211> LENGTH: 323
<212> TYPE: PRT
<213> ORGANISM: Xenopus laevis

<400> SEQUENCE: 6

Met Leu Leu Ser Lys Phe Gly Ser Leu Ala His Ile Cys Asn Pro Ser
 1               5                  10                  15

Asn Met Glu His Leu Pro Val Lys Ile Leu Gln Pro Val Lys Val Asp
            20                  25                  30

Lys Glu Pro Phe Glu Lys Val Tyr Gln Val Gly Ser Val Val Ala Ser
            35                  40                  45

Gly Gly Phe Gly Thr Val Tyr Ser Asp Ser Arg Ile Ala Asp Gly Gln
        50                  55                  60

Pro Val Ala Val Lys His Val Ala Lys Glu Arg Val Thr Glu Trp Gly
 65                  70                  75                  80

Thr Leu Asn Gly Val Met Val Pro Leu Glu Ile Val Leu Leu Lys Lys
                85                  90                  95

Val Pro Thr Ala Phe Arg Gly Val Ile Asn Leu Leu Asp Trp Tyr Glu
            100                 105                 110

Arg Pro Asp Ala Phe Leu Ile Val Met Glu Arg Pro Glu Pro Val Lys
            115                 120                 125

Asp Leu Phe Asp Tyr Ile Thr Glu Lys Gly Pro Leu Asp Glu Asp Thr
    130                 135                 140

Ala Arg Gly Phe Phe Arg Gln Val Leu Glu Ala Val Arg His Cys Tyr
145                 150                 155                 160

Asn Cys Gly Val Val His Arg Asp Ile Lys Asp Glu Asn Leu Leu Val
                165                 170                 175

Asp Thr Arg Asn Gly Glu Leu Lys Leu Ile Asp Phe Gly Ser Gly Ala
            180                 185                 190

Leu Leu Lys Asp Thr Val Tyr Thr Asp Phe Asp Gly Thr Arg Val Tyr
            195                 200                 205

Ser Pro Pro Glu Trp Val Arg Tyr His Arg Tyr His Gly Arg Ser Ala
    210                 215                 220

Thr Val Trp Ser Leu Gly Val Leu Leu Tyr Asp Met Val Tyr Gly Asp
225                 230                 235                 240

Ile Pro Phe Glu Gln Asp Glu Glu Ile Val Arg Val Arg Leu Cys Phe
                245                 250                 255

Arg Arg Arg Ile Ser Thr Glu Cys Gln Gln Leu Ile Lys Trp Cys Leu
            260                 265                 270

Ser Leu Arg Pro Ser Asp Arg Pro Thr Leu Glu Gln Ile Phe Asp His
        275                 280                 285

Pro Trp Met Cys Lys Cys Asp Leu Val Lys Ser Glu Asp Cys Asp Leu
    290                 295                 300

Arg Leu Arg Thr Ile Asp Asn Asp Ser Ser Thr Ser Ser Ser Ser Asn
305                 310                 315                 320

Glu Ser Leu

```
<210> SEQ ID NO 7
<211> LENGTH: 313
<212> TYPE: PRT
<213> ORGANISM: Mus musculus

<400> SEQUENCE: 7

Met Leu Leu Ser Lys Ile Asn Ser Leu Ala His Leu Arg Ala Arg Pro
  1               5                  10                  15

Cys Asn Asp Leu His Ala Thr Lys Leu Ala Pro Gly Lys Glu Lys Glu
                 20                  25                  30

Pro Leu Glu Ser Gln Tyr Gln Val Gly Pro Leu Leu Gly Ser Gly Gly
             35                  40                  45

Phe Gly Ser Val Tyr Ser Gly Ile Arg Val Ala Asp Asn Leu Pro Val
 50                  55                  60

Ala Ile Lys His Val Glu Lys Asp Arg Ile Ser Asp Trp Gly Glu Leu
 65                  70                  75                  80

Pro Asn Gly Thr Arg Val Pro Met Glu Val Val Leu Leu Lys Lys Val
                 85                  90                  95

Ser Ser Asp Phe Ser Gly Val Ile Arg Leu Leu Asp Trp Phe Glu Arg
                100                 105                 110

Pro Asp Ser Phe Val Leu Ile Leu Glu Arg Pro Glu Pro Val Gln Asp
            115                 120                 125

Leu Phe Asp Phe Ile Thr Glu Arg Gly Ala Leu Gln Glu Asp Leu Ala
130                 135                 140

Arg Gly Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Ser Arg Gly Glu Ile Lys Leu Ile Asp Phe Gly Ser Gly Ala Leu
            180                 185                 190

Leu Lys Asp Thr Val Tyr Thr Asp Phe Asp Gly Thr Arg Val Tyr Ser
            195                 200                 205

Pro Pro Glu Trp Ile Arg Tyr His Arg Tyr His Gly Arg Ser Ala Ala
210                 215                 220

Val Trp Ser Leu Gly Ile Leu Leu Tyr Asp Met Val Cys Gly Asp Ile
225                 230                 235                 240

Pro Phe Glu His Asp Glu Ile Ile Lys Gly Gln Val Phe Phe Arg
                245                 250                 255

Gln Thr Val Ser Ser Glu Cys Gln His Leu Ile Lys Trp Cys Leu Ser
                260                 265                 270

Leu Arg Pro Ser Asp Arg Pro Ser Phe Glu Glu Ile Arg Asn His Pro
            275                 280                 285

Trp Met Gln Gly Asp Leu Leu Pro Gln Ala Ala Ser Glu Ile His Leu
290                 295                 300

His Ser Leu Ser Pro Gly Ser Ser Lys
305                 310

<210> SEQ ID NO 8
<211> LENGTH: 313
<212> TYPE: PRT
<213> ORGANISM: Rattus norvegicus

<400> SEQUENCE: 8

Met Leu Leu Ser Lys Ile Asn Ser Leu Ala His Leu Arg Ala Ala Pro
  1               5                  10                  15
```

-continued

```
Cys Asn Asp Leu His Ala Asn Lys Leu Ala Pro Gly Lys Glu Lys Glu
             20                  25                  30

Pro Leu Glu Ser Gln Tyr Gln Val Gly Pro Leu Leu Gly Ser Gly Gly
         35                  40                  45

Phe Gly Ser Val Tyr Ser Gly Ile Arg Val Ala Asp Asn Leu Pro Val
     50                  55                  60

Ala Ile Lys His Val Glu Lys Asp Arg Ile Ser Asp Trp Gly Glu Leu
 65                  70                  75                  80

Pro Asn Gly Thr Arg Val Pro Met Glu Val Val Leu Leu Lys Lys Val
                 85                  90                  95

Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125

Leu Phe Asp Phe Ile Thr Glu Arg Gly Ala Leu Gln Glu Glu Leu Ala
    130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Glu Ile Val Lys Gly Gln Val Tyr Phe Arg
                245                 250                 255

Gln Arg Val Ser Ser Glu Cys Gln His Leu Ile Arg Trp Cys Leu Ser
            260                 265                 270

Leu Arg Pro Ser Asp Arg Pro Ser Phe Glu Glu Ile Gln Asn His Pro
        275                 280                 285

Trp Met Gln Asp Val Leu Leu Pro Gln Ala Thr Ala Glu Ile His Leu
    290                 295                 300

His Ser Leu Ser Pro Ser Pro Ser Lys
305                 310

<210> SEQ ID NO 9
<211> LENGTH: 313
<212> TYPE: PRT
<213> ORGANISM: Homo sapiens

<400> SEQUENCE: 9

Met Leu Leu Ser Lys Ile Asn Ser Leu Ala His Leu Arg Ala Ala Pro
  1               5                  10                  15

Cys Asn Asp Leu His Ala Thr Lys Leu Ala Pro Gly Lys Glu Lys Glu
             20                  25                  30

Pro Leu Glu Ser Gln Tyr Gln Val Gly Pro Leu Leu Gly Ser Gly Gly
         35                  40                  45

Phe Gly Ser Val Tyr Ser Gly Ile Arg Val Ser Asp Asn Leu Pro Val
     50                  55                  60

Ala Ile Lys His Val Glu Lys Asp Arg Ile Ser Asp Trp Gly Glu Leu
 65                  70                  75                  80
```

```
Pro Asn Gly Thr Arg Val Pro Met Glu Val Leu Leu Lys Lys Val
                85                  90                  95

Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125

Leu Phe Asp Phe Ile Thr Glu Arg Gly Ala Leu Gln Glu Glu Leu Ala
    130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:antisense
      oligonucleotide complementary to the region
      surrounding the translational start site of HKID-1
      mRNA

<400> SEQUENCE: 10
agagcagcat cgcgggcgac ggc                                        23

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:antisense
      oligonucleotide complementary to the region
      surrounding the translational start site of HKID-1
      mRNA

<400> SEQUENCE: 11
agcagcatcg cgggcgac                                              18
```

MOLECULES OF THE HKID-1-RELATED PROTEIN FAMILY AND USES THEREOF

CROSS-REFERENCE TO RELATED APPLICATION

This application is a divisional of U.S. application Ser. No. 09/237,543, filed Jan. 26, 1999, now U.S. Pat. No. 6,143,540 which is herein incorporated by reference.

BACKGROUND OF THE INVENTION

Protein kinases play critical roles in the regulation of biochemical and morphological changes associated with cellular growth and division (D'Urso, G. et al. (1990) *Science* 250: 786–791; Birchmeier. C. et al. (1993) *Bioessays* 15: 185–189). They serve as growth factor receptors and signal transducers and have been implicated in cellular transformation and malignancy (Hunter, T. et al. (1992) *Cell* 70: 375–387; Posada, J. et al. (1992) *Mol. Biol. Cell* 3: 583–592; Hunter, T. et al. (1994) *Cell* 79: 573–582). For example, protein kinases have been shown to participate in the transmission of signals from growth-factor receptors (Sturgill, T. W. et al. (1988) *Nature* 344: 715–718; Gomez, N. et al. (1991) *Nature* 353: 170–173), control of entry of cells into mitosis (Nurse, P. (1990) *Nature* 344: 503–508; Maller, J. L. (1991) *Curr. Opin. Cell Biol.* 3: 269–275) and regulation of actin bundling (Husain-Chishti, A. et al. (1988) *Nature* 334: 718–721). Protein kinases can be divided into two main groups based on either amino acid sequence similarity or specificity for either serine/threonine or tyrosine residues. A small number of dual-specificity kinases are structurally like the serine/threonine-specific group. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks, S. K. et al. (1988) *Science* 241: 42–52). Rat KID-1 is a serine/threonine protein kinase that is induced by membrane depolarization or forskolin but not by neurotrophins or growth factors (Feldman, J. D. et al. (1998). *J. Biol. Chem.* 273:16535–16543). Rat KID-1 is induced in specific regions of the hippocampus and cortex in response to kainic acid and electroconvulsive shock, suggesting that rat KID-1 is involved in neuronal function, synaptic plasticity, learning, and memory as well as kainic acid seizures and some nervous system-related diseases such as seizures and epilepsy. Rat KID-1 paralogs include the PIM-1 proteins known to be proto-oncogenes. The present invention is based, at least in part, on the discovery of the human species ortholog of rat KID-1, termed HKID-1.

SUMMARY OF THE INVENTION

The present invention is based, at least in part, on the discovery of a gene encoding HKID-1, an intracellular protein that is predicted to be a member of the serine/threonine protein kinase superfamily. Based on this, the present invention provides isolated HKID-1 proteins and nucleic acid molecules encoding HKID-1 proteins. The present invention also provides methods of detecting HKID-1 protein or HKID-1 nucleic acids and methods for identifying modulators of HKID-1 protein or HKID-1 nucleic acids.

BRIEF DESCRIPTION OF THE DRAWINGS

FIGS. 1A and 1B depicts the sequence (SEQ ID NO:1) and predicted amino acid sequence (SEQ ID NO:2) of human HKID-1. The open reading frame of SEQ ID NO:1 extends from nucleotide 171 to nucleotide 1259 (SEQ ID NO:3).

FIG. 2 depicts an alignment of a portion of the amino acid sequence of HKID-1 (SEQ ID NO:29; corresponds to amino acids 40 to 293 of SEQ ID NO:2) and a eukaryotic protein kinase domain consensus sequence derived from a hidden Markov model (PF00069; SEQ ID NO:28). The upper sequence in the alignment is the PF00069 sequence while the lower sequence is amino acid 40 to amino acid 293 of SEQ ID NO:2.

FIG. 4 shows a polypeptide sequence alignment, carried out with the MegAlign program of the DNASTAR sequence analysis package using the J. Hein method with a PAM250 residue weight table, of the HKID-1 polypeptide sequence of SEQ ID NO:2 and rat KID-1 (AF086624; SEQ ID NO:37), *Xenopus laevis* (frog) PIM-1 (Q91822; SEQ ID NO:38), murine PIM-1 (P06803; SEQ ID NO:39), rat PIM-1 (P26794; SEQ ID NO:40), and human PIM-1 (P11309; SEQ ID NO:41).

DETAILED DESCRIPTION OF THE INVENTION

Figure 3:
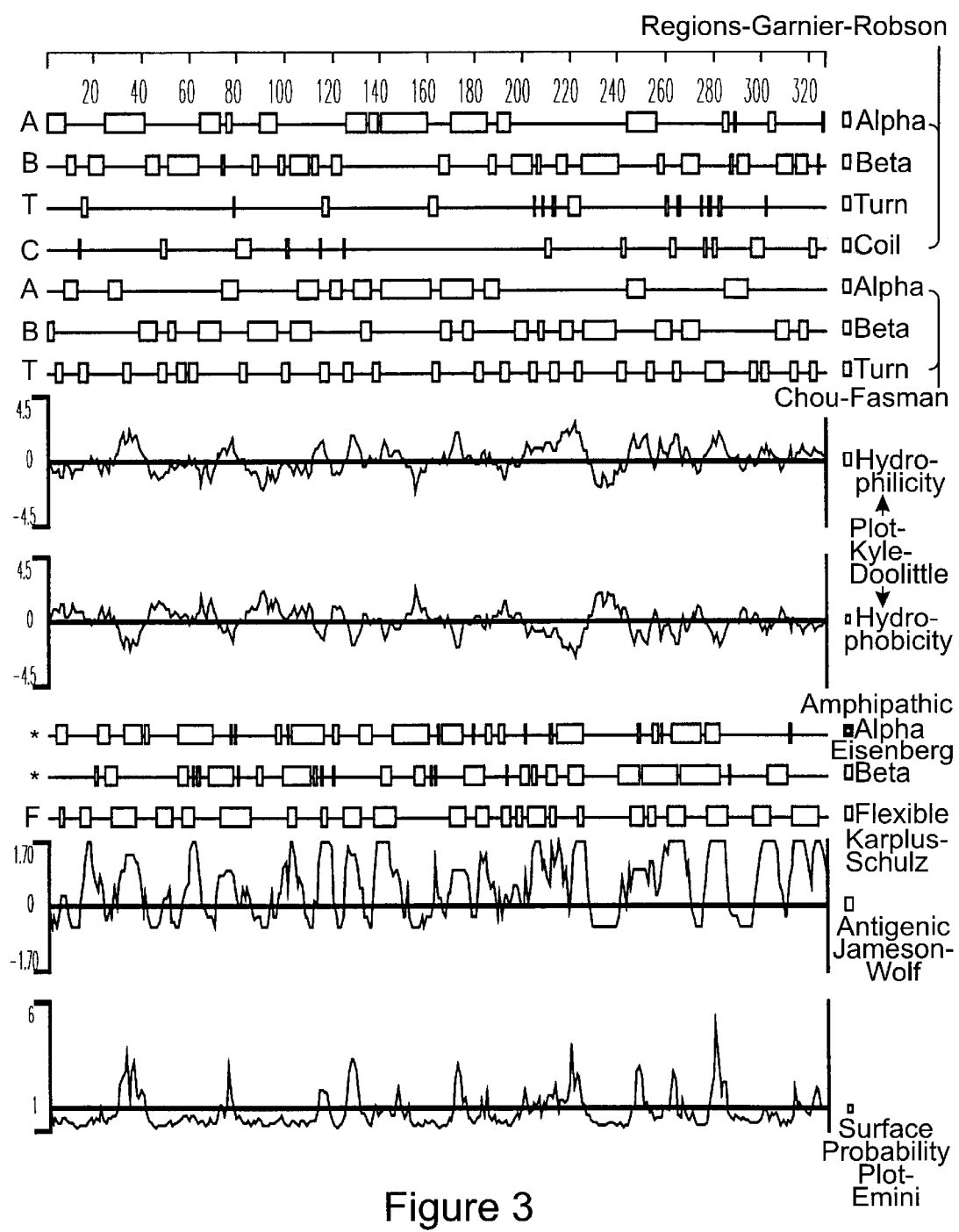
FIG. 3 shows a Protean analysis of the HKID-1 amino acid sequence of SEQ ID NO:2. Shown are: alpha, beta, turn and coil regions identified with the Garnier-Robson algorithm; alpha, beta and turn regions identified with the Chou-Fasman algorithm; hydrophilicity and hydrophobicity plots generated with the Kyte-Doolittle algorithm; alpha amphipathic and beta amphipathic regions identified with the Eisenberg algorithm; flexible regions identified with the Karplus-Schulz algorithm; the antigenic index calculated using the Jameson-Wolf algorithm; and a surface probability plot calculated using the Emini algorithm. For the hydrophobicity plot, relative hydrophobicity is shown above the dotted line, and relative hydrophilicity is shown below the dotted line.

The present invention is based on the discovery of a cDNA molecule encoding human HKID-1, a member of the serine/threonine kinase superfamily. A nucleotide sequence encoding a human HKID-1 protein is shown in FIG. 1 (SEQ ID NO:1; SEQ ID NO:3 includes the open reading frame only). A predicted amino acid sequence of HKID-1 protein is also shown in FIG. 1 (SEQ ID NO:2).

The HKID-1 protein of SEQ ID NO:2 is predicted to possess the following sites or domains: one cAMP- and cGMP-dependent protein kinase phosphorylation site (PS00004; SEQ ID NO:4) from amino acids 260–263 of SEQ ID NO:2; SEQ ID NO:5; three protein kinase C phosphorylation sites (PS00005; SEQ ID NO:6) from amino acids 137–139, 275–277, and 279–281, of SEQ ID NO:2; SEQ ID NOS:7–9; three casein kinase II phosphorylation sites (PS00006; SEQ ID NO:10) from amino acids 202–205, 211–214, and 321–324, of SEQ ID NO:2; SEQ ID NOS:11–13; one tyrosine kinase phosphorylation site (PS00007; SEQ ID NO:14) from amino acid 33–40, of SEQ ID NO:2; SEQ ID NO:15; seven N-myristoylation sites (PS00008; SEQ ID NO:16) from amino acids 43–48, 49–54, 57–62, 63–68, 80–85, 98–103, and 295–300 of SEQ ID NO:2; SEQ ID NOS:17–23; one protein kinase ATP-binding region signature (PS00107; SEQ ID NO:24) from amino acid 46–54, of SEQ ID NO:2; SEQ ID NO:25; one serine/threonine protein kinase active site signature (PS00108; SEQ ID NO:26) from amino acid 166–178, of SEQ ID NO:2; SEQ ID NO:27; and one eukaryotic protein kinase domain consensus derived from a hidden Markov model (HMM) (PF00069; SEQ ID NO:28) from amino acid 40–293, of SEQ ID NO:2; SEQ ID NO:29. For general information regarding PFAM identifiers, PS prefix and PF prefix domain identification numbers, refer to Sonnhammer et al. (1997) *Protein* 28:405–420 and http://www.psc.edu/general/software/packages/pfam/pfam.html.

The HKID-1 polypeptide sequence of SEQ ID NO:2 was analyzed with the MEMSAT transmembrane domain prediction software. MEMSAT predicted three potential transmembrane domains in the HKID-1 polypeptide sequence of SEQ ID NO:2: amino acid 42 to 58 (SEQ ID NO:42), amino acid 78 to 94 (SEQ ID NO:43), and amino acid 226 to 245 (SEQ ID NO:44). Because the rat ortholog of HKID-1, rat KID-1, is known to be a soluble protein, it is likely that the potential transmembrane domains predicted by MEMSAT represent hydrophobic domains of HKID-1 protein involved in hydrophobic interactions in the core of the HKID-1 protein and not transmembrane domains.

In an embodiment of the invention, the HKID-1 molecules are protein kinases which are expressed and/or function in cells of the nervous system, as a nonlimiting example, cells of the hippocampus and cortex.

As used herein, the term "protein kinase" includes a protein or polypeptide which is capable of modulating its own phosphorylation state or the phosphorylation state of another protein or polypeptide. Protein kinases can have a specificity for (i.e., a specificity to phosphorylate) serine/threonine residues, tyrosine residues, or both serine/threonine and tyrosine residues, e.g., the dual specificity kinases. Specificity of a protein kinase for phosphorylation of either tyrosine or serine/threonine can be predicted by the sequence of two of the subdomains, VIb and VIII, (described in, for example, Hanks et al. (1988) *Science* 241:42–52, the contents of which are incorporated herein by reference).

Protein kinases play a role in signaling pathways associated with cells expressing them. Thus, since the HKID-1 molecules are expressed in neuronal cells, HKID-1 may be involved in: 1) nervous system disorders; 2) seizures; 3) epilepsy; 4) learning; 5) memory; or 6) synaptic plasticity. HKID-1 may also be involved in proliferative disorders, such as cancer, because HKID-1 is the paralog of the PIM-1 proteins which are known to be proto-oncogenes.

Various aspects of the invention are described in further detail in the following subsections.

I. Isolated Nucleic Acid Molecules

The HKID-1 cDNA sequence (SEQ ID NO:1), which is approximately 2126 nucleotides long including untranslated regions, contains a predicted methionine-initiated coding sequence of 978 base pairs (nucleotides 171–1259 of SEQ ID NO:1; SEQ ID NO:3) encoding a 326 amino acid protein (SEQ ID NO:2) having a predicted molecular weight of approximately 35.86 kDa (excluding post-translational modifications) (FIG. 1).

One aspect of the invention provides isolated nucleic acid molecules that encode HKID-1 proteins or biologically active portions thereof, as well as nucleic acid molecules sufficient for use as hybridization probes to identify HKID-1-encoding nucleic acids (e.g., HKID-1 mRNA) and fragments for use as PCR primers for the amplification or mutation of HKID-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences (preferably protein encoding sequences) which naturally flank the nucleic acid (i.e., sequences located at the 5' and 3' ends of the nucleic acid) in the genomic DNA of the organism from which the nucleic acid is derived. For example; in various embodiments, the isolated HKID-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

An isolated nucleic acid molecule of the present invention, e.g., a nucleic acid molecule having the nucleotide sequence of SEQ ID NO:1 or SEQ ID NO:3, or a complement of any of these nucleotide sequences, can be isolated using standard molecular biology techniques and the sequence information provided herein. Using all or a portion of the nucleic acid sequences of SEQ ID NO:1 or SEQ ID NO:3, as a hybridization probe, HKID-1 nucleic acid molecules can be isolated using standard hybridization and cloning techniques (e.g., as described in Sambrook et al., eds., *Molecular Cloning: A Laboratory Manual*, 2nd ed., Cold Spring Harbor Laboratory, Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to HKID-1 nucleotide sequences can be prepared by standard synthetic techniques, e.g., using an automated DNA synthesizer.

The invention features an isolated nucleic acid molecule which is at least 26% (or 30%, 35%, 40%, 45%, 55%, 65%, 75%, 85%, 95%, or 98%) identical to the nucleotide sequence shown in SEQ ID NO:1 or a complement thereof. The invention also features an isolated nucleic acid molecule which is at least 43% (or 45%, 50%, 55%, 65%, 75%, 85%, 95%, or 98%) identical to the nucleotide sequence shown in SEQ ID NO:3 or a complement thereof.

The invention also features an isolated nucleic acid molecule which includes a nucleotide sequence encoding a protein having an amino acid sequence that is at least 95.5% (or 95.8%, 96%, 96.5%, 97%, 98% or 99%) identical to the amino acid sequence of SEQ ID NO:2.

In an embodiment, an isolated HKID-1 nucleic acid molecule has the nucleotide sequence shown SEQ ID NO:1 or SEQ ID NO:3.

Also within the invention is an isolated nucleic acid molecule which encodes a fragment of a polypeptide having the amino acid sequence of SEQ ID NO:2, the fragment including at least 15 (or 25, 30, 50, 100, 150, 200, 250, 270, 290, 310 or 326) contiguous amino acids of SEQ ID NO:2.

Moreover, the isolated nucleic acid molecule of the invention can comprise only a portion of an isolated nucleic acid sequence encoding HKID-1, for example, a fragment which can be used as a probe or primer or a fragment encoding a biologically active portion of HKID-1, for example, fragments comprising nucleotides 306 to 332 of SEQ ID NO:1, encoding the protein kinase ATP-binding region signature domain of HKID-1, nucleotides 666 to 704 of SEQ ID NO:1, encoding the serine/threonine protein kinase active site signature domain of HKID-1, and nucleotides 288 to 1049 of SEQ ID NO:1 encoding the eukaryotic protein kinase domain of HKID-1.

The nucleotide sequence determined from the human HKID-1 gene and/or cDNA allows for the generation of probes and primers designed for use in identifying and/or cloning HKID-1 homologs in other cell types, e.g., from other tissues, as well as HKID-1 orthologs and homologs from other mammals. The probe/primer typically comprises a substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense sequence of SEQ ID NO:1 or SEQ ID NO:3, or of a naturally occurring mutant and/or allelelic variant of SEQ ID NO:1 or SEQ ID NO:3.

Probes based on the human HKID-1 nucleotide sequence can be used to detect transcripts, cDNAs, or genomic sequences encoding the same or identical proteins or allelic variants thereof. The probe comprises a label group attached thereto, e.g., a radioisotope, a fluorescent compound, an enzyme, or an enzyme co-factor. Such probes can be used as part of a diagnostic test kit for identifying cells or tissues which mis-express an HKID-1 protein, such as by measuring levels of an HKID-1-encoding nucleic acid in a sample of cells from a subject, e.g., detecting HKID-1 mRNA levels or determining whether a genomic HKID-1 gene has been mutated or deleted.

Another embodiment of the invention features isolated HKID-1 nucleic acid molecules which specifically detect HKID-1 nucleic acid molecules relative to nucleic acid molecules encoding other members of the serine/threonine protein kinase superfamily. For example, in one embodiment, an isolated HKID-1 nucleic acid molecule hybridizes under stringent conditions to a nucleic acid molecule comprising the nucleotide sequence of SEQ ID NO:1, SEQ ID NO:3, or a complement thereof. In another embodiment, an isolated HKID-1 nucleic acid molecule is at least 547 (or 550, 600, 650, 700, 800, 900, 1000, 1100, 1200, 1300, 1400, 1500, 1600, 1700, 1800, 1900, 2000, 2100, 2126 or 2200) nucleotides in length and hybridizes under stringent conditions to a nucleic acid molecule comprising the nucleotide sequence shown in SEQ ID NO:1, SEQ ID NO:3, or a complement thereof. In another embodiment, an isolated HKID-1 nucleic acid molecule comprises nucleotides 306 to 332 of SEQ ID NO:1, encoding the protein kinase ATP-binding region signature domain of HKID-1, or a complement thereof. In yet another embodiment, an isolated HKID-1 nucleic acid molecule comprises nucleotides 666 to 704 of SEQ ID NO:1, encoding the serine/threonine protein kinase active site signature domain of HKID-1, or a complement thereof. In another embodiment, an isolated HKID-1 nucleic acid molecule comprises nucleotides 288 to 1049 of SEQ ID NO:1 encoding the eukaryotic protein kinase domain of HKID-1, or a complement thereof. In another embodiment, the invention provides an isolated nucleic acid molecule which is antisense to the coding strand of an HKID-1 nucleic acid.

An isolated nucleic acid fragment encoding a "biologically active portion of HKID-1" can be prepared by isolating a portion of SEQ ID NO:1 or SEQ ID NO:3, expressing the encoded portion of HKID-1 protein (e.g., by recombinant expression in vitro) and assessing the activity of the encoded portion of HKID-1. For example, an isolated nucleic acid fragment encoding a biologically active portion of HKID-1 includes one or more of a cAMP- and cGMP-dependent protein kinase phosphorylation site (PS00004; SEQ ID NO:4), for example, from amino acids 260–263 of SEQ ID NO:2; SEQ ID NO:5; a protein kinase C phosphorylation site (PS00005; SEQ ID NO:6), for example, from amino acids 137–139, 275–277, and 279–281, of SEQ ID NO:2; SEQ ID NOS:7–9; a casein kinase II phosphorylation site (PS00006; SEQ ID NO:10), for example, from amino acids 202–205, 211–214, and 321–324, of SEQ ID NO:2; SEQ ID NOS: 11–13; a tyrosine kinase phosphorylation site (PS00007; SEQ ID NO:14), for example, from amino acid 33–40, of SEQ ID NO:2; SEQ ID NO:15; an N-myristoylation sites (PS00008; SEQ ID NO:16) from amino acids 43–48, 49–54, 57–62, 63–68, 80–85, 98–103, and 295–300 of SEQ ID NO:2; SEQ ID NOS:17–23; a protein kinase ATP-binding region signature (PS00107; SEQ ID NO:24), for example, from amino acid 46–54, of SEQ ID NO:2; SEQ ID NO:25; a serine/threonine protein kinase active site signature (PS00108; SEQ ID NO:26), for example, from amino acid 166–178, of SEQ ID NO:2; SEQ ID NO:27; and a eukaryotic protein kinase domain (PF00069; SEQ ID NO:28), for example, from amino acid 40–293, of SEQ ID NO:2; SEQ ID NO:29.

The invention further encompasses isolated nucleic acid molecules that differ from the nucleotide sequence of SEQ ID NO:1 or SEQ ID NO:3 due to degeneracy of the genetic code and thus encode the same HKID-1 protein as that encoded by the nucleotide sequence shown in SEQ ID NO:1 or SEQ ID NO:3.

In addition to the human HKID-1 nucleotide sequence shown in SEQ ID NO:1 or SEQ ID NO:3, it will be appreciated by those skilled in the art that DNA sequence polymorphisms that lead to changes in the amino acid sequences of HKID-1 may exist within a population (e.g., the human population). Such genetic polymorphism in the HKID-1 gene may exist among individuals within a population due to natural allelic variation. An allele is one of a group of genes which occur alternatively at a given genetic locus. As used herein, the terms "gene" and "recombinant gene" refer to nucleic acid molecules comprising an open reading frame encoding an HKID-1 protein, preferably a mammalian HKID-1 protein. As used herein, the phrase "allelic variant" refers to a nucleotide sequence which occurs at an HKID-1 locus or to a polypeptide encoded by the nucleotide sequence. Such natural allelic variations can typically result in 1–5% variance in the nucleotide sequence of the HKID-1 gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations in HKID-1 that are the result of natural allelic variation and that do not alter the functional activity of HKID-1 are intended to be within the scope of the invention. Allelic variants of HKID-1 will physically and genetically map to the HKID-1 genetic and physical locus shown in Example 5 to be chromosome 22 between the D22S1169 and D22S__qter markers, 196.70 centiRays from the top of the chromosome 22 linkage group.

The invention includes an isolated nucleic acid molecule which encodes a naturally occurring allelic variant, encoding a fully functional protein, a partially functional HKID-1 protein, or a non functional protein, of a polypeptide comprising the amino acid sequence of SEQ ID NO:2, wherein the nucleic acid molecule hybridizes to a nucleic acid molecule comprising SEQ ID NO:1, SEQ ID NO:3, or a complement thereof under stringent conditions.

Moreover, isolated nucleic acid molecules encoding HKID-1 proteins from other species (HKID-1 homologs or orthologs), which have a nucleotide sequence which differs from that of a human HKID-1, are intended to be within the scope of the invention, excluding those known in the art, e.g., the rat and *Xenopus laevis* (frog) species orthologs of HKID-1. Nucleic acid molecules corresponding to natural allelic variants, homologs, and orthologs of the HKID-1 cDNA of the invention can be isolated based on their identity to the human HKID-1 nucleic acids disclosed herein using the human cDNAs, or a portion thereof, as a hybridization probe according to standard hybridization techniques under stringent hybridization conditions. Orthologs of HKID-1 will often map to genetic loci that are syntenic with the human HKID-1 genetic and physical locus shown in Example 5 to be chromosome 22 between the D22S1169 and D22S_qter markers, 196.70 centiRays from the top of the chromosome 22 linkage group.

In another embodiment of the invention, an isolated nucleic acid molecule of the invention is 1) at least 547 (or 550, 600, 650, 700, 800, 900, 1000, 1100, 1200, 1300, 1400, 1500, 1600, 1700, 1800, 1900, 2000, 2100 or 2126) nucleotides of the nucleotide sequence shown in SEQ ID NO:1; or 2) at least 415 (or 450, 500, 550, 600, 650, 700, 800, 900 or 978) nucleotides of the nucleotide sequence shown in SEQ ID NO:3; or 3) at least 8 (or 10, 15, 20, 25, 35, 45, 65, 85, 105, 125, 175, 225, 275, 325, 375, 400, 450, 500, 550, 600, 650, 700, 750, 800, 850, 900 or 923) nucleotides from nucleotide 1–923 of SEQ ID NO:1; SEQ ID NO:30; or 4) at least 8 (or 10, 15, 20, 25, 35, 45, 65, 85, 105, 125, 175, 225, 275, 325 or 344) nucleotides from nucleotide 1–344 of SEQ ID NO:3; SEQ ID NO:3 1 and hybridizes under stringent conditions to the nucleic acid molecule comprising the nucleotide sequence, preferably the coding sequence, of SEQ ID NO:1, SEQ ID NO:3, or a complement thereof.

In another embodiment, an isolated nucleic acid molecule of the invention comprises a nucleic acid molecule which is a complement of the nucleotide sequence shown in SEQ ID NO:1 or SEQ ID NO:3, or a portion thereof. A nucleic acid molecule which is complementary to a given nucleotide sequence is one which is sufficiently complementary to the given nucleotide sequence that it can hybridize to the given nucleotide sequence under stringent conditions.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, SEQ ID NO:3, or the complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the HKID-1 sequence that may exist in the population, the skilled artisan will further appreciate that changes can be introduced by mutation into the nucleotide sequence of SEQ ID NO:1 or SEQ ID NO:3, thereby leading to changes in the amino acid sequence of the encoded HKID-1 protein, without altering the biological activity of the HKID-1 protein. For example, one can make nucleotide substitutions leading to amino acid substitutions at "non-essential" amino acid residues. A "non-essential" amino acid residue is a residue that can be altered from the wild-type sequence of HKID-1 (e.g., the sequence of SEQ ID NO:2) without altering the biological activity, whereas an "essential" amino acid residue is required for biological activity. For example, amino acid residues that are not conserved or only semi-conserved among HKID-1 of various species may be non-essential for activity and thus would be likely targets for alteration. Alternatively, amino acid residues that are conserved among the HKID-1 proteins of various species may be essential for activity and thus would not be likely targets for alteration.

For example, HKID-1 proteins of the present invention contain at least one conserved protein kinase ATP-binding region signature (PS00107; SEQ ID NO:24) from amino acid 46–54, of SEQ ID NO:2; SEQ ID NO:25; at least one conserved serine/threonine protein kinase active site signature (PS00108; SEQ ID NO:26) from amino acid 166–178, of SEQ ID NO:2; SEQ ID NO:27; and at least one conserved eukaryotic protein kinase domain (PF00069; SEQ ID NO:28) from amino acid 40–293, of SEQ ID NO:2; SEQ ID NO:29. For example, HKID-1 proteins of the present invention may contain at least one conserved or nonconserved cAMP- and cGMP-dependent protein kinase phosphorylation site (PS00004; SEQ ID NO:4), for example, from amino acids 260–263 of SEQ ID NO:2; SEQ ID NO:5; protein kinase C phosphorylation site (PS00005; SEQ ID NO:6), for example, from amino acids 137–139, 275–277, and 279–281, of SEQ ID NO:2; SEQ ID NOS:7–9; casein kinase II phosphorylation site (PS00006; SEQ ID NO:10), for example, from amino acids 202–205, 211–214, and 321–324, of SEQ ID NO:2; SEQ ID NOS:11–13; tyrosine kinase phosphorylation site (PS00007; SEQ ID NO:14), for example, from amino acid 33–40, of SEQ ID NO:2; SEQ ID NO:15; N-myristoylation site (PS00008; SEQ ID NO:16), for example, from amino acids 43–48, 49–54, 57–62, 63–68, 80–85, 98–103, and 295–300 of SEQ ID NO:2; SEQ ID NOS:17–23.

Accordingly, another aspect of the invention provides nucleic acid molecules encoding HKID-1 proteins that contain changes in amino acid residues that are not essential for activity. Such HKID-1 proteins differ in amino acid sequence from SEQ ID NO:2 yet retain biological activity. In one embodiment, the isolated nucleic acid molecule includes a nucleotide sequence encoding a protein that includes an amino acid sequence that is at least about 45%, 55%, 65%, 75%, 85%, 95%, or 98% identical to the amino acid sequence of SEQ ID NO:2.

An isolated nucleic acid molecule encoding an HKID-1 protein having a sequence which differs from that of SEQ ID NO:2 can be created by introducing one or more nucleotide substitutions, additions or deletions into the nucleotide sequence of SEQ ID NO:1 or SEQ ID NO:3, such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in HKID-1 is preferably replaced with another amino acid residue from the same side chain family. Alternatively, mutations can be introduced randomly along all or part of an HKID-1 coding sequence, such as by saturation mutagenesis, and the resultant mutants can be screened for HKID-1 biological activity to identify mutants that retain activity. Following mutagenesis, the encoded protein can be expressed recombinantly and the activity of the protein can be determined.

In an embodiment, a mutant HKID-1 can be assayed for (1) the ability to be phosphorylated by protein kinases, (2) the ability to be N-myristoylated, (3) the ability to bind ATP, (4) the ability to phosphorylate proteins, and (5) the ability to phosphorylate proteins specifically on serine and threonine residues. In another embodiment, mutant HKID-1 can be assayed for its ability to play a role in signaling pathways associated with cells that express HKID-1, e.g. Cellos of the nervous system, the ability to form protein-protein interaction with its substrate proteins expressed in cells in which HKID-1 is expressed, and the ability to form protein-protein interactions with proteins in the signal transduction and biological pathways that exist in cells in which HKID-1 is expressed.

The present invention further encompasses antisense nucleic acid molecules, i.e., molecules which are complementary to a sense nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire HKID-1 coding strand, or to only a portion thereof, e.g., all or part of the protein coding region (or open reading frame). An antisense nucleic acid molecule can be antisense to a noncoding region of the coding strand of a nucleotide sequence encoding HKID-1. The noncoding regions ("5' and 3' untranslated regions") are the 5' and 3' sequences which flank the coding region and are not translated into amino acids.

Given the coding strand sequences encoding HKID-1 disclosed herein (e.g., SEQ ID NO:1 or SEQ ID NO:3), antisense nucleic acids of the invention can be designed according to the rules of Watson and Crick base pairing. The antisense nucleic acid molecule can be complementary to the entire coding region of HKID-1 mRNA, but more preferably is an oligonucleotide which is antisense to only a portion of the coding or noncoding region of HKID-1 mRNA. For example, the antisense oligonucleotide can be complementary to the region surrounding the translation start site of HKID-1 mRNA, e.g., an oligonucleotide having the sequence AGAGCAGCATCGCGGGCGACGGC (SEQ ID NO:35) or AGCAGCATCGCGGGCGAC (SEQ ID NO:36). An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an HKID-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.*

15:6131–6148) or a chimeric RNA-DNA analogue (Inoue et al. (1987) *FEBS Lett*. 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave HKID-1 mRNA transcripts to thereby inhibit translation of HKID-1 mRNA. A ribozyme having specificity for an HKID-1-encoding nucleic acid can be designed based upon the nucleotide sequence of an HKID-1 cDNA disclosed herein (e.g., SEQ ID NO:1, SEQ ID NO:3). For example, a derivative of a Tetrahymena L-19 IVS RNA can be constructed in which the nucleotide sequence of the active site is complementary to the nucleotide sequence to be cleaved in an HKID-1-encoding mRNA. See, e.g., Cech et al. U.S. Pat. No. 4,987,071; and Cech et al. U.S. Pat. No. 5,116,742. Alternatively, HKID-1 mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules which form triple helical structures. For example, HKID-1 gene expression can be inhibited by targeting nucleotide sequences complementary to the regulatory region of the HKID-1 (e.g., the HKID-1 promoter and/or enhancers) to form triple helical structures that prevent transcription of the HKID-1 gene in target cells. See generally Helene (1991) *Anticancer Drug Des*. 6(6):569; Helene (1992) *Ann. N.Y Acad. Sci*. 660:27; and Maher (1992) Bioassays 14(12):807.

In embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670.

PNAs of HKID-1 can be used in therapeutic and diagnostic applications. For example, PNAs can be used as antisense or antigene agents for sequence-specific modulation of gene expression by, e.g., inducing transcription or translation arrest or inhibiting replication. PNAs of HKID-1 can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996), supra).

In another embodiment, PNAs of HKID-1 can be modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra, Finn et al. (1996) *Nucleic Acids Res*. 24(17):3357–63, Mag et al. (1989) *Nucleic Acids Res*. 17:5973, and Peterser et al. (1975) *Bioorganic Med. Chem. Lett*. 5:1119.

II. Isolated HKID-1 Proteins

One aspect of the invention provides isolated HKID-1 proteins, and biologically active portions thereof, as well as polypeptide fragments suitable for use as immunogens to raise anti-HKID-1 antibodies. In one embodiment, native HKID-1 proteins can be isolated from cells or tissue sources by an appropriate purification scheme using standard protein purification techniques. In another embodiment, HKID-1 proteins are produced by recombinant DNA techniques. Alternative to recombinant expression, an HKID-1 protein or polypeptide can be synthesized chemically using standard peptide synthesis techniques.

An "isolated" or "purified" protein or biologically active portion thereof is substantially free of cellular material or other contaminating proteins from the cell or tissue source from which the HKID-1 protein is derived, or substantially free of chemical precursors or other chemicals when chemically synthesized. The language "substantially free of cellular material" includes preparations of HKID-1 protein in which the protein is separated from cellular components of the cells from which it is isolated or recombinantly produced. Thus, HKID-1 protein that is substantially free of cellular material includes preparations of HKID-1 protein having less than about 30%, 20%, 10%, or 5% (by dry weight) of non-HKID-1 protein (also referred to herein as a "contaminating protein"). When the HKID-1 protein or biologically active portion thereof is recombinantly produced, it is also preferably substantially free of culture medium, i.e., culture medium represents less than about 20%, 10%, or 5% of the volume of the protein preparation. When HKID-1 protein is produced by chemical synthesis, it is preferably substantially free of chemical precursors or other chemicals, i.e., it is separated from chemical precursors or other chemicals which are involved in the synthesis of the protein. Accordingly such preparations of HKID-1 protein have less than about 30%, 20%, 10%, 5% (by dry weight) of chemical precursors or non-HKID-1 chemicals.

In one embodiment, the isolated proteins of the present invention, preferably HKID-1 proteins, are identified based on the presence in them of at least one "protein kinase ATP-binding site" and at least one "serine/threonine protein kinase active site" and that they have an amino acid sequence which is at least 60%, 65%, 70%, 75%, 80%, 81%, 85%, 90%, 95%, 99% or more homologous to an amino acid sequence including SEQ ID NO:2. As used herein, the term "protein kinase ATP-binding site" includes an amino acid sequence with significant amino acid sequence similarity to the protein kinase ATP-binding region signature sequence (PS00107) of SEQ ID NO:24 which is conserved in protein kinases. As used herein, the term "serine/threonine protein kinase active site" includes an amino acid sequence with significant amino acid sequence similarity to the serine/threonine protein kinase active site signature sequence (PS00 108) of SEQ ID NO:26 which is conserved in protein kinases that phosphorylate serine and threonine residues on proteins.

In another embodiment, the isolated proteins of the present invention, preferably HKID-1 proteins, are identified based on the presence of at least one eukaryotic protein kinase domain and that they have an amino acid sequence which is at least 60%, 65%, 70%, 75%, 80%, 81%, 85%, 90%, 95%, 99% or more homologous to an amino acid sequence including SEQ ID NO:2. As used herein, the term "eukaryotic protein kinase domain" includes an amino acid sequence with significant amino acid sequence similarity to the eukaryotic protein kinase domain sequence (PF00069) of SEQ ID NO:28 which is conserved in protein kinases.

Yet another embodiment of the invention includes an isolated HKID-1 protein which is encoded by a nucleic acid molecule having a nucleotide sequence that is at least about 43% (or 45%, 50%, 55%, 65%, 75%, 85%, 95%, or 98%) identical to SEQ ID NO:3; an isolated HKID-1 protein which is encoded by a nucleic acid molecule having a nucleotide sequence at least about 65%, preferably 65%, 70%, 75%, 80%, 85%, 90%, 95% or 99% identical to the portions of SEQ ID NO:1 encoding the cAMP- and cGMP-dependent protein kinase phosphorylation site (PS00004; SEQ ID NO:4) from amino acids 260–263 of SEQ ID NO:2; SEQ ID NO:5; the three protein kinase C phosphorylation sites (PS00005; SEQ ID NO:6) from amino acids 137–139, 275–277, and 279–281, of SEQ ID NO:2; SEQ ID NOS:7–9; the three casein kinase II phosphorylation sites (PS00006; SEQ ID NO:10) from amino acids 202–205, 211–214, and 321–324, of SEQ ID NO:2; SEQ ID NOS:11–13; the tyrosine kinase phosphorylation site (PS00007; SEQ ID NO:14) from amino acid 33–40, of SEQ ID NO:2; SEQ ID NO:15; the seven N-myristoylation sites (PS00008; SEQ ID NO:16) from amino acids 43–48, 49–54, 57–62, 63–68, 80–85, 98–103, and 295–300 of SEQ ID NO:2; SEQ ID NOS:17–23; and an isolated HKID-1 protein which is encoded by a nucleic acid molecule having a nucleotide sequence at least about 65%, preferably 65%, 70%, 75%, 80%, 85%, 90%, 95% or 99% identical to the portions of SEQ ID NO:1 encoding the protein kinase ATP-binding region signature (PS00107; SEQ ID NO:24) from amino acid 46–54, of SEQ ID NO:2; SEQ ID NO:25 (e.g., about nucleotides 306 to 332 of SEQ ID NO:1; SEQ ID NO:32); the serine/threonine protein kinase active site signature (PS00108; SEQ ID NO:26) from amino acid 166–178, of SEQ ID NO:2; SEQ ID NO:27 (e.g., about nucleotides 666 to 704 of SEQ ID NO:1; SEQ ID NO:33); and the eukaryotic protein kinase domain (PF00069; SEQ ID NO:28) from amino acid 40–293, of SEQ ID NO:2; SEQ ID NO:29 (e.g., about nucleotides 288 to 1049 of SEQ ID NO:1; SEQ ID NO:34) and an isolated HKID-1 protein which is encoded by a nucleic acid molecule having a nucleotide sequence which hybridizes under stringent hybridization conditions to a nucleic acid molecule having the nucleotide sequence of SEQ ID NO:3, or the complement thereof.

Biologically active portions of an HKID-1 protein include peptides comprising amino acid sequences sufficiently identical to or derived from the amino acid sequence of the HKID-1 protein (e.g., the amino acid sequence shown in SEQ ID NO:2), which include fewer amino acids than the full length HKID-1 proteins, and exhibit at least one activity of an HKID-1 protein. Typically, biologically active portions comprise a domain or motif with at least one activity of the HKID-1 protein. A biologically active portion of an HKID-1 protein can be a polypeptide which is, for example, 10, 25, 50, 100 or more amino acids in length. Biologically active polypeptides include one or more identified HKID-1 structural domains, e.g., a cAMP- and cGMP-dependent protein kinase phosphorylation site (PS00004; SEQ ID NO:4), for example, from amino acids 260–263 of SEQ ID NO:2; SEQ ID NO:5; a protein kinase C phosphorylation site (PS00005; SEQ ID NO:6), for example, from amino acids 137–139, 275–277, and 279–281, of SEQ ID NO:2; SEQ ID NOS:7–9; a casein kinase II phosphorylation site (PS00006; SEQ ID NO:10), for example, from amino acids 202–205, 211–214, and 321–324, of SEQ ID NO:2; SEQ ID NOS:11–13; a tyrosine kinase phosphorylation site (PS00007; SEQ ID NO:14), for example, from amino acid 33–40, of SEQ ID NO:2; SEQ ID NO:15; an N-myristoylation site (PS00008; SEQ ID NO:16), for example, from amino acids 43–48, 49–54, 57–62, 63–68, 80–85, 98–103, and 295–300 of SEQ ID NO:2; SEQ ID NOS:17–23; a protein kinase ATP-binding region signature (PS00107; SEQ ID NO:24), for example, from amino acid 46–54, of SEQ ID NO:2; SEQ ID NO:25; a serine/threonine protein kinase active site signature (PS00108; SEQ ID NO:26), for example, from amino acid 166–178, of SEQ ID NO:2; SEQ ID NO:27; and an eukaryotic protein kinase domain (PF00069; SEQ ID NO:28), for example, from amino acid 40–293, of SEQ ID NO:2; SEQ ID NO:29.

Moreover, other biologically active portions, in which other regions of the protein are deleted, can be prepared by recombinant techniques and evaluated for one or more of the functional activities of a native HKID-1 protein.

HKID-1 protein has the amino acid sequence shown of SEQ ID NO:2. Other useful HKID-1 proteins are substantially identical to SEQ ID NO:2 and retain the functional activity of the protein of SEQ ID NO:2 yet differ in amino acid sequence due to natural allelic variation or mutagenesis. For example, such HKID-1 proteins and polypeptides posses at least one biological activity described herein such as, (1) the ability to be phosphorylated by protein kinases, (2) the ability to be N-myristoylated, (3) the ability to bind ATP, (4) the ability to phosphorylate proteins, (5) the ability to phosphorylate proteins specifically on serine and threonine residues, (6) the ability to play a role in signaling pathways associated with cells that express HKID-1, e.g. Cellos of the nervous system, (7) the ability to form protein-protein interaction with its substrate proteins expressed in cells in which HKID-1 is expressed, and (8) the ability to form protein-protein interactions with proteins in the signal transduction and biological pathways that exist in cells in which HKID-1 is expressed. Accordingly, a useful isolated HKID-1 protein is a protein which includes an amino acid sequence at least about 45%, preferably 55%, 65%, 75%, 85%, 95%, or 99% identical to the amino acid sequence of SEQ ID NO:2 and retains the functional activity of the HKID-1 proteins of SEQ ID NO:2. In other instances, the HKID-1 protein is a protein having an amino acid sequence 55%, 65%, 75%, 85%, 95%, or 98% identical to one or more of the HKID-1 domains including one cAMP- and cGMP-dependent protein kinase phosphorylation site (PS00004; SEQ ID NO:4) from amino acids 260–263 of SEQ ID NO:2; SEQ ID NO:5; three protein kinase C phosphorylation sites (PS00005; SEQ ID NO:6) from amino acids 137–139, 275–277, and 279–281, of SEQ ID NO:2; SEQ ID NOS:7–9; three casein kinase II phosphorylation sites (PS00006; SEQ ID NO:10) from amino acids 202–205, 211–214, and 321–324, of SEQ ID NO:2; SEQ ID NOS:11–13; one tyrosine kinase phosphorylation site (PS00007; SEQ ID NO:14) from amino acid 33–40, of SEQ ID NO:2; SEQ ID NO:15; seven N-myristoylation sites (PS00008; SEQ ID NO:16) from amino acids 43–48, 49–54, 57–62, 63–68, 80–85, 98–103, and 295–300 of SEQ ID NO:2; SEQ ID NOS:17–23; one protein kinase ATP-binding region signature (PS00107; SEQ ID NO:24) from amino acid 46–54, of SEQ ID NO:2; SEQ ID NO:25; one serine/threonine protein kinase active site signature (PS00108; SEQ ID NO:26) from amino acid 166–178, of SEQ ID NO:2; SEQ ID NO:27; and one eukaryotic protein kinase domain (PF00069; SEQ ID NO:28) from amino acid 40–293, of SEQ ID NO:2; SEQ ID NO:29. In an embodiment, the HKID-1 protein retains a functional activity of the HKID-1 protein of SEQ ID NO:2.

To determine the percent identity of two amino acid sequences or two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., percent identity=number of identical positions/total number of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403. BLAST nucleotide searches can be performed with the NBLAST program, score=100, wordlength=12 to obtain nucleotide sequences homologous to HKID-1 nucleic acid molecules of the invention. BLAST protein searches can be performed with the XBLAST program, score=50, wordlength=3 to obtain amino acid sequences homologous to HKID-1 protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search which detects distant relationships between molecules. Altschul et al. (1997) supra. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides HKID-1 chimeric or fusion proteins. As used herein, an HKID-1 "chimeric protein" or "fusion protein" comprises an HKID-1 polypeptide operably linked to a non-HKID-1 polypeptide. A "HKID-1 polypeptide" refers to a polypeptide having an amino acid sequence corresponding to HKID-1, whereas a "non-HKID-1 polypeptide" refers to a polypeptide having an amino acid sequence corresponding to a protein which is not substantially identical to the HKID-1 protein, e.g., a protein which is different from the HKID-1 protein and which is derived from the same or a different organism. Within an HKID-1 fusion protein the HKID-1 polypeptide can correspond to all or a portion of an HKID-1 protein, preferably at least one biologically active portion of an HKID-1 protein. Within the fusion protein, the term "operably linked" is intended to indicate that the HKID-1 polypeptide and the non-HKID-1 polypeptide are fused in-frame to each other. The non-HKID-1 polypeptide can be fused to the N-terminus or C-terminus of the HKID-1 polypeptide.

One useful isolated fusion protein is a GST-HKID-1 fusion protein in which the HKID-1 sequences are fused to the C-terminus of the GST sequences. Such fusion proteins can facilitate the purification of recombinant HKID-1.

In another embodiment, the fusion protein is an HKID-1 protein containing an heterologous signal sequence at its N-terminus. In certain host cells (e.g., mammalian host cells), expression and/or secretion of HKID-1 can be increased through use of a heterologous signal sequence. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an HKID-1-immunoglobulin fusion protein in which all or part of HKID-1 is fused to sequences derived from a member of the immunoglobulin protein family.

Preferably, an HKID-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). An HKID-1-encoding nucleic acid can be cloned into such an expression vector such that the fusion moiety is linked in-frame to the HKID-1 protein.

The present invention also provides variants of the HKID-1 proteins (i.e., proteins having a sequence which differs from that of the HKID-1 amino acid sequence). Such variants can function as either HKID-1 agonists (mimetics) or as HKID-1 antagonists. Variants of the HKID-1 protein can be generated by mutagenesis, e.g., discrete point mutation or truncation of the HKID-1 protein. An agonist of the HKID-1 protein can retain substantially the same, or a subset, of the biological activities of the naturally occurring form of the HKID-1 protein, e.g., (1) the ability to be phosphorylated by protein kinases, (2) the ability to be N-myristoylated, (3) the ability to bind ATP, (4) the ability to phosphorylate proteins, (5) the ability to phosphorylate proteins specifically on serine and threonine residues, (6) the ability to play a role in signaling pathways associated with cells that express HKID-1, e.g. Cellos of the nervous system, (7) the ability to form protein-protein interaction with its substrate proteins expressed in cells in which HKID-1 is expressed, and (8) the ability to form protein-protein interactions with proteins in the signal transduction and biological pathways that exist in cells in which HKID-1 is expressed. An antagonist of the HKID-1 protein can inhibit one or more of the activities of the naturally occurring form of the HKID-1 protein by, for example, competitively binding to a downstream or upstream member of a cellular signaling cascade which includes the HKID-1 protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the HKID-1 proteins.

Variants of the HKID-1 protein which function as either HKID-1 agonists (mimetics) or as HKID-1 antagonists can be identified by screening combinatorial libraries of mutants, e.g., truncation mutants, of the HKID-1 protein for HKID-1 protein agonist or antagonist activity. In one embodiment, a variegated library of HKID-1 variants is generated by combinatorial mutagenesis at the nucleic acid level and is encoded by a variegated gene library. A variegated library of HKID-1 variants can be produced by, for example, enzymatically ligating a mixture of synthetic oligonucleotides into gene sequences such that a degenerate set of potential HKID-1 sequences is expressible as individual polypeptides, or alternatively, as a set of larger fusion proteins (e.g., for phage display) containing the set of HKID-1 sequences therein. There are a variety of methods which can be used to produce libraries of potential HKID-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential HKID-1 sequences. Methods for synthesizing degenerate oligonucleotides are known in the art (see, e.g., Narang (1983) Tetrahedron 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the HKID-1 protein coding sequence can be used to generate a variegated population of HKID-1 fragments for screening and subsequent selection of variants of an HKID-1 protein. In one embodiment, a library of coding sequence fragments can be generated by treating a double stranded PCR fragment of an HKID-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the HKID-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of HKID-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify HKID-1 variants (Arkin and Yourvan (1992) *Proc. Natl. Acad. Sci. USA* 89:7811–7815; Delgrave et al. (1993) *Protein Engineering* 6(3):327–331).

Also within the invention is an isolated polypeptide which is a naturally occurring allelic variant, comprising a fully functional protein, a partially functional protein, or a non functional protein, of a polypeptide that includes the amino acid sequence of SEQ ID NO:2, wherein the polypeptide is encoded by a nucleic acid molecule which hybridizes to a nucleic acid molecule comprising SEQ ID NO:1, SEQ ID NO:3 or a complement thereof under stringent conditions. The allelic variants of HKID-1 will be encoded by a gene that will physically and genetically map to the HKID-1 genetic and physical locus shown in Example 5 to be chromosome 22 between the D22S1169 and D22S_qter markers, 196.70 centiRays from the top of the chromosome 22 linkage group.

Also within the invention is an isolated polypeptide which is a species ortholog of HKID-1, a polypeptide that includes the amino acid sequence of SEQ ID NO:2, wherein the polypeptide is encoded by a nucleic acid molecule which hybridizes to a nucleic acid molecule comprising SEQ ID NO:1, SEQ ID NO:3 or a complement thereof under stringent conditions. Species orthologs of HKID-1 will often physically and genetically map to the region of the genome of the species from which they originate that is syntenic to human chromosome 22 between the D22S1169 and D22S_qter markers, 196.70 centiRays from the top of the chromosome 22 linkage group.

III. Anti-HKID-1 Antibodies

The present invention further provides antibodies that bind to the HKID-1 proteins of the present invention. The term "antibody" as used herein refers to immunoglobulin molecules and immunologically active portions of immunoglobulin molecules, i.e., molecules that contain an antigen binding site which specifically binds an antigen, such as HKID-1. A molecule which specifically binds to HKID-1 is a molecule which binds HKID-1, but does not substantially bind other molecules in a sample, e.g., a biological sample, which naturally contains HKID-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind HKID-1. The term "monoclonal antibody" or "monoclonal antibody composition", as used herein, refers to a population of antibody molecules that contain only one species of an antigen binding site capable of immunoreacting with a particular epitope of HKID-1. A monoclonal antibody composition thus typically displays a single binding affinity for a particular HKID-1 protein with which it immunoreacts.

An isolated HKID-1 protein, or a portion or fragment thereof, can be used as an immunogen to generate antibodies that bind HKID-1 using standard techniques for polyclonal and monoclonal antibody preparation. The full-length HKID-1 protein can be used or, alternatively, the invention provides antigenic peptide fragments of HKID-1 for use as immunogens. The antigenic peptide of HKID-1 comprises at least 8 (preferably 10, 15, 20, or 30) amino acid residues of the amino acid sequence shown in SEQ ID NO:2 and encompasses an epitope of HKID-1 such that an antibody raised against the peptide forms a specific immune complex with HKID-1.

Epitopes encompassed by the antigenic peptide are regions of HKID-1 that are located on the surface of the protein. A surface probability analysis, presented in FIG. 3, of the polypeptide sequence (SEQ ID NO:2) of human HKID-1 protein identifies probable antigenic regions; amino acid 28 to 39, amino acid 124 to 129, and amino acid 277 to 283 are particularly likely to be localized to the surface of the protein and, therefore, are likely to encode surface residues useful for targeting antibody production.

AN HKID-1 immunogen typically is used to prepare antibodies by immunizing a suitable subject, (e.g., rabbit, goat, mouse or other mammal) with the immunogen. An appropriate immunogenic preparation can contain, for example, recombinantly expressed HKID-1 protein or a chemically synthesized HKID-1 polypeptide. The preparation can further include an adjuvant, such as Freund's complete or incomplete adjuvant, or similar immunostimulatory agent. Immunization of a suitable subject with an immunogenic HKID-1 preparation induces a polyclonal anti-HKID-1 antibody response.

Polyclonal anti-HKID-1 antibodies can be prepared as described above by immunizing a suitable subject with an HKID-1 immunogen. The anti-HKID-1 antibody titer in the immunized subject can be monitored over time by standard techniques, such as with an enzyme linked immunosorbent assay (ELISA) using immobilized HKID-1. If desired, the antibody molecules directed against HKID-1 can be isolated from the mammal (e.g., from the blood) and further purified by well-known techniques, such as protein A chromatography to obtain the IgG fraction. At an appropriate time after immunization, e.g., when the anti-HKID-1 antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with an HKID-1 immunogen as described above, and the culture supernatants of the resulting hybridoma cells are screened to identify a hybridoma producing a monoclonal antibody that binds HKID-1.

Any of the many well known protocols used for fusing lymphocytes and immortalized cell lines can be applied for the purpose of generating an anti-HKID-1 monoclonal antibody (see, e.g., *Current Protocols in Immunology*, supra; Galfre et al. (1977) *Nature* 266:55052; R. H. Kenneth, in *Monoclonal Antibodies: A New Dimension In Biological Analyses*, Plenum Publishing Corp., New York, N.Y. (1980); and Lerner (1981) *Yale J. Biol. Med.*, 54:387–402. Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line, e.g., a myeloma cell line that is sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind HKID-1, e.g., using a standard ELISA assay.

Alternative to preparing monoclonal antibody-secreting hybridomas, a monoclonal anti-HKID-1 antibody can be identified and isolated by screening a recombinant combinatorial immunoglobulin library (e.g., an antibody phage display library) with HKID-1 to thereby isolate immunoglobulin library members that bind HKID-1. Kits for generating and screening phage display libraries are commercially available (e.g., the Pharmacia *Recombinant Phage Antibody System*, Catalog No. 27–9400–01; and the Stratagene SurfZAP™ *Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-HKID-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559; Morrison (1985) *Science* 229:1202–1207; Oi et al. (1986)

*Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of HKID-1. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope.

First, a non-human monoclonal antibody which binds a selected antigen (epitope), e.g., an antibody which inhibits HKID-1 activity, is identified. The heavy chain and the light chain of the non-human antibody are cloned and used to create phage display Fab fragments. For example, the heavy chain gene can be cloned into a plasmid vector so that the heavy chain can be secreted from bacteria. The light chain gene can be cloned into a phage coat protein gene so that the light chain can be expressed on the surface of phage. A repertoire (random collection) of human light chains fused to phage is used to infect the bacteria which express the non-human heavy chain. The resulting progeny phage display hybrid antibodies (human light chain/non-human heavy chain). The selected antigen is used in a panning screen to select phage which bind the selected antigen. Several rounds of selection may be required to identify such phage. Next, human light chain genes are isolated from the selected phage which bind the selected antigen. These selected human light chain genes are then used to guide the selection of human heavy chain genes as follows. The selected human light chain genes are inserted into vectors for expression by bacteria. Bacteria expressing the selected human light chains are infected with a repertoire of human heavy chains fused to phage. The resulting progeny phage display human antibodies (human light chain/human heavy chain).

Next, the selected antigen is used in a panning screen to select phage which bind the selected antigen. The phage selected in this step display a completely human antibody which recognizes the same epitope recognized by the original selected, non-human monoclonal antibody. The genes encoding both the heavy and light chains are readily isolated and can be further manipulated for production of human antibody. This technology is described by Jespers et al. (1994, *Bio/technology* 12:899–903).

An anti-HKID-1 antibody (e.g., monoclonal antibody) can be used to isolate HKID-1 by standard techniques, such as affinity chromatography or immunoprecipitation. An anti-HKID-1 antibody can facilitate the purification of natural HKID-1 from cells and of recombinantly produced HKID-1 expressed in host cells. Moreover, an anti-HKID-1 antibody can be used to detect HKID-1 protein (e.g., in a cellular lysate or cell supernatant) in order to evaluate the abundance and pattern of expression of the HKID-1 protein. Anti-HKID-1 antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

IV. Recombinant Expression Vectors and Host Cells

The invention further provides vectors, preferably expression vectors, containing a nucleic acid encoding an HKID-1 protein of the present invention or a portion thereof.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., HKID-1 proteins, mutant forms of HKID-1, fusion proteins, etc.).

The recombinant expression vectors of the invention can be designed for expression of HKID-1 in prokaryotic or eukaryotic cells, e.g., bacterial cells such as *E. coli*, insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the HKID-1 expression vector is a yeast expression vector. Examples of vectors for expression in yeast S. cerivisae include pYepSec1 (Baldari et al. (1987) *EMBO J.* 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and pPicZ (InVitrogen Corp, San Diego, Calif.).

Alternatively, HKID-1 can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to HKID-1 mRNA. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention provides host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, HKID-1 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Selectable markers include those which confer resistance to drugs, such as G418, hygromycin and methotrexate. Nucleic acid encoding a selectable marker can be introduced into a host cell on the same vector as that encoding HKID-1 or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) HKID-1 protein. Accordingly, the invention further provides methods for producing HKID-1 protein using the host cells of the invention. In one embodiment, the method comprises culturing the host cell of invention (into which a recombinant expression vector encoding HKID-1 has been introduced) in a suitable medium such that HKID-1 protein is produced. In another embodiment, the method further comprises isolating HKID-1 from the medium or the host cell.

The host cells of the invention can also be used to produce nonhuman transgenic animals. For example, in one embodiment, a host cell of the invention is a fertilized oocyte or an embryonic stem cell into which HKID-1-coding sequences have been introduced. Such host cells can then be used to create non-human transgenic animals in which exogenous HKID-1 sequences have been introduced into their genome or homologous recombinant animals in which endogenous HKID-1 sequences have been altered. Such animals are useful for studying the function and/or activity of HKID-1 and for identifying and/or evaluating modulators of HKID-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous HKID-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing HKID-1-encoding nucleic acid into the male pronuclei of a fertilized oocyte, e.g., by microinjection, retroviral infection, and allowing the oocyte to develop in a pseudopregnant female foster animal. The HKID-1 cDNA sequence (e.g., that of SEQ ID NO:1 or SEQ ID NO:3) can be introduced as a transgene into the genome of a non-human animal. Alternatively, a nonhuman homolog of the human HKID-1 gene, such as a mouse HKID-1 gene, can be isolated based on hybridization to the human HKID-1 cDNA and used as a transgene. Intronic sequences and polyadenylation signals can also be included in the transgene to increase the efficiency of expression of the transgene. A tissue-specific regulatory sequence(s) can be operably linked to the HKID-1 transgene to direct expression of HKID-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the HKID-1 transgene in its genome and/or expression of HKID-1 mRNA in tissues or cells of the animals. A transgenic founder animal can then be used to breed additional animals carrying the transgene. Moreover, transgenic animals carrying a transgene encoding HKID-1 can further be bred to other transgenic animals carrying other transgenes.

To create an homologous recombinant animal, a vector is prepared which contains at least a portion of an HKID-1 gene (e.g., a human or a non-human homolog of the HKID-1 gene, e.g., a murine HKID-1 gene) into which a deletion, addition or substitution has been introduced to thereby alter, e.g., functionally disrupt, the HKID-1 gene. In an embodiment, the vector is designed such that, upon homologous recombination, the endogenous HKID-1 gene is functionally disrupted (i.e., no longer encodes a functional protein; also referred to as a "knock out" vector). Alternatively, the vector can be designed such that, upon homologous recombination, the endogenous HKID-1 gene is mutated or otherwise altered but still encodes functional protein (e.g., the upstream regulatory region can be altered to thereby alter the expression of the endogenous HKID-1 protein). In the homologous recombination vector, the altered portion of the HKID-1 gene is flanked at its 5' and 3' ends by additional nucleic acid of the HKID-1 gene to allow for homologous recombination to occur between the exogenous HKID-1 gene carried by the vector and an endogenous HKID-1 gene in an embryonic stem cell. The additional flanking HKID-1 nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced HKID-1 gene has homologously recombined with the endogenous HKID-1 gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach*, Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of Saccharomyces cerevisiae (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

V. Pharmaceutical Compositions

The HKID-1 nucleic acid molecules, HKID-1 proteins, and anti-HKID-1 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an HKID-1 protein or anti-HKID-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Depending on the type and severity of the disease, about 1 $\mu$g/kg to 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 $\mu$g/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g. Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

VI. Uses and Methods of the Invention

The nucleic acid molecules, proteins, protein homologs, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). An HKID-1 protein interacts with other cellular proteins and can thus be used as a target for developing therapeutic molecules for modulating HKID-1 protein in cells expressing HKID-1 protein or cells involved in the HKID-1 pathway, e.g., cells of the nervous system. The isolated nucleic acid molecules of the invention can be used to express HKID-1 protein (e.g., via a recombinant expression vector in a host cell in gene therapy applications), to detect HKID-1 mRNA (e.g., in a biological sample) or a genetic lesion in an HKID-1 gene, and to modulate HKID-1 activity. In addition, the HKID-1 proteins can be used to screen drugs or compounds which modulate the HKID-1 activity or expression as well as to treat disorders characterized by insufficient or excessive production of HKID-1 protein or production of HKID-1 protein forms which have decreased or aberrant activity compared to HKID-1 wild type protein. In addition, the anti-HKID-1 antibodies of the invention can be used to detect and isolate HKID-1 proteins and modulate HKID-1 activity.

This invention further provides novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to HKID-1 proteins or have a stimulatory or inhibitory effect on, for example, HKID-1 expression or HKD-1 activity.

In one embodiment, the invention provides assays for screening candidate or test compounds which bind to or modulate the activity of an HKID-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckennann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *BioTechniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223, 409), plasmids (Cull et al. (1992) *Proc. Natl. Acad. Sci. USA* 89:1865–1869) or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

In an embodiment, an assay of the present invention is a cell-free assay comprising contacting an HKID-1 protein or biologically active portion thereof with a test compound and determining the ability of the test compound to bind to the HKID-1 protein or biologically active portion thereof. Binding of the test compound to the HKID-1 protein can be determined either directly or indirectly as described above. In an embodiment, the assay includes contacting the HKID-1 protein or biologically active portion thereof with a known compound which binds HKID-1 to form an assay mixture, contacting the assay mixture with a test compound, and determining the ability of the test compound to interact with an HKID-1 protein, wherein determining the ability of the test compound to interact with an HKID-1 protein comprises determining the ability of the test compound to preferentially bind to HKID-1 or biologically active portion thereof as compared to the known compound.

In another embodiment, an assay is a cell-free assay comprising contacting HKID-1 protein or biologically active portion thereof with a test compound and determining the ability of the test compound to modulate (e.g., stimulate or inhibit) the activity of the HKID-1 protein or biologically active portion thereof. Determining the ability of the test compound to modulate the activity of HKID-1 can be accomplished, for example, by determining the ability of the HKID-1 protein to bind to an HKID-1 target molecule by one of the methods described above for determining direct binding. In an alternative embodiment, determining the ability of the test compound to modulate the activity of HKID-1 can be accomplished by determining the ability of the HKID-1 protein to further modulate an HKID-1 target molecule. For example, the catalytic/enzymatic activity of the target molecule on an appropriate substrate can be determined as previously described.

In yet another embodiment, the cell-free assay comprises contacting the HKID-1 protein or biologically active portion thereof with a known compound which binds HKID-1 to form an assay mixture, contacting the assay mixture with a test compound, and determining the ability of the test compound to interact with an HKID-1 protein, wherein determining the ability of the test compound to interact with an HKID-1 protein comprises determining the ability of the HKID-1 protein to preferentially bind to or modulate the activity of an HKID-1 target molecule.

Phosphoaminoacid analysis of the phosphorylated substrate can also be performed in order to determine which residues on the HKID-1 substrate are phosphorylated. Briefly, the radiophosphorylated protein band can be excised from the SDS gel and subjected to partial acid hydrolysis. The products can then be separated by one-dimensional electrophoresis and analyzed on, for example, a phospho-imager and compared to ninhydrin-stained phosphoaminoacid standards.

In yet another embodiment of the invention, the cell free assay determines the ability of the HKID-1 protein to phosphorylate an HKID-1 target molecule by, for example, an in vitro kinase assay. Briefly, an HKID-1 target molecule, e.g., an immunoprecipitated HKID-1 target molecule from a cell line expressing such a molecule, can be incubated with the HKID-1 protein and radioactive ATP, e.g., [gamma-$^{32}$P] ATP, in a buffer containing $MgCl_2$ and $MnCl_2$, e.g., 10 mM $MgCl_2$ and 5 mM $MnCl_2$. Following the incubation, the immunoprecipitated HKID-1 target molecule can be separated by SDS-polyacrylamide gel electrophoresis under reducing conditions, transferred to a membrane, e.g., a PVDF membrane, and autoradiographed. The appearance of detectable bands on the autoradiograph indicates that the HKID-1 substrate has been phosphorylated.

In one embodiment, an assay is a cell-based assay in which a cell which expresses a soluble form of HKID-1 protein, or a biologically active portion thereof, is contacted with a test compound and the ability of the test compound to bind to an HKID-1 protein determined. The cell, for example, can be a yeast cell or a cell of mammalian origin. Determining the ability of the test compound to bind to the HKID-1 protein can be accomplished, for example, by coupling the test compound with a radioisotope or enzymatic label such that binding of the test compound to the HKID-1 protein or biologically active portion thereof can be determined by detecting the labeled compound in a complex. For example, test compounds can be labeled with $^{125}$I, $^{35}$S, $^{14}$C, or $^{3}$H, either directly or indirectly, and the radio-isotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In an embodiment, the assay comprises contacting a cell which expresses a soluble form of HKID-1 protein, or a biologically active portion thereof, on the cell surface with a known compound which binds HKID-1 to form an assay mixture, contacting the assay mixture with a test compound, and determining the ability of the test compound to interact with an HKID-1 protein, wherein determining the ability of the test compound to interact with an HKID-1 protein comprises determining the ability of the test compound to preferentially bind to HKID-1 or a biologically active portion thereof as compared to the known compound.

In another embodiment, an assay is a cell-based assay comprising contacting a cell expressing a soluble form of HKID-1 protein, or a biologically active portion thereof, with a test compound and determining the ability of the test compound to modulate (e.g., stimulate or inhibit) the activity of the HKID-1 protein or biologically active portion thereof. Determining the ability of the test compound to modulate the activity of HKID-1 or a biologically active portion thereof can be accomplished, for example, by determining the ability of the HKID-1 protein to bind to or interact with an HKID-1 target molecule. As used herein, a "target molecule" is a molecule with which an HKID-1 protein binds or interacts in nature, for example, a substrate molecule phosphorylated by HKID-1 protein in the interior of a cell which expresses an HKID-1 protein, a molecule associated with the internal surface of a cell membrane or a cytoplasmic molecule. An HKID-1 target molecule can be a non-HKID-1 molecule or an HKID-1 protein or polypeptide of the present invention. In one embodiment, an HKID-1 target molecule is a component of a signal transduction pathway which mediates transduction of a signal.

Determining the ability of the HKID-1 protein to bind to or interact with an HKID-1 target molecule can be accomplished by one of the methods described above for determining direct binding. In an embodiment, determining the ability of the HKID-1 protein to bind to or interact with an HKID-1 target molecule can be accomplished by determining the activity of the target molecule. For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., an HKID-1-responsive regulatory element operably linked to a nucleic acid encoding a detectable marker, e.g. luciferase), or detecting a cellular response, for example, cellular differentiation, or cell proliferation.

In various formats of the assay methods of the present invention, it may be desirable to immobilize either HKID-1 or its target molecule to facilitate separation of complexed from uncomplexed forms of one or both of the proteins, as well as to accommodate automation of the assay. Binding of a test compound to HKID-1, or interaction of HKID-1 with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/HKID-1 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or HKID-1 protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of HKID-1 binding or activity determined using standard techniques.

Other techniques for immobilizing proteins on matrices can also be used in the screening assays of the invention. For example, either HKID-1 or its target molecule can be immobilized utilizing conjugation of biotin and streptavidin. Biotinylated HKID-1 or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemicals). Alternatively, antibodies reactive with HKID-1 or target molecules but which do not interfere with binding of the HKID-1 protein to its target molecule can be derivatized to the wells of the plate, and unbound target or HKID-1 trapped in the wells by antibody conjugation. Methods for detecting such complexes, in addition to those described above for the GST-immobilized complexes, include immunodetection of complexes using antibodies reactive with the HKID-1 or target molecule, as well as enzyme-linked assays which rely on detecting an enzymatic activity associated with the HKID-1 or target molecule.

In another embodiment, modulators of HKID-1 expression are identified in a method in which a cell is contacted with a candidate compound and the expression of HKID-1 mRNA or protein in the cell is determined. The level of expression of HKID-1 mRNA or protein in the presence of the candidate compound is compared to the level of expression of HKID-1 mRNA or protein in the absence of the candidate compound. The candidate compound can then be identified as a modulator of HKID-1 expression based on this comparison. For example, when expression of HKID-1 mRNA or protein is greater (statistically significantly greater) in the presence of the candidate compound than in its absence, the candidate compound is identified as a stimulator of HKID-1 mRNA or protein expression. Alternatively, when expression of HKID-1 mRNA or protein is less (statistically significantly less) in the presence of the candidate compound than in its absence, the candidate compound is identified as an inhibitor of HKID-1 mRNA or protein expression. The level of HKID-1 mRNA or protein expression in the cells can be determined by methods described herein for detecting HKID-1 mRNA or protein.

In yet another aspect of the invention, the HKID-1 proteins can be used as "bait proteins" in a two-hybrid assay or three hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with HKID-1 ("HKID-1-binding proteins" or "HKID-1-bp") and modulate HKID-1 activity. Such HKID-1-binding proteins are also likely to be involved in the propagation of signals by the HKID-1 proteins as, for example, upstream or downstream elements of the HKID-1 pathway. The invention also provides for the use of proteins that interact with HKID-1, e.g., two-hybrid interactors with HKID-1, as baits in two-hybrid screens and the identification of HKID-1 interacting protein interacting proteins. HKID-1 interacting protein interacting proteins are likely to be involved in the HKID-1 signal transduction pathway.

This invention further provides novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Tissue Typing

The HKID-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the HKID-1 sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The HKID-1 sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from HKID-1 sequences described herein is used to generate a unique identification database for an individual, those same reagents can later be used to identify tissue from that individual. Using the unique identification database, positive identification of the individual, living or dead, can be made from extremely small tissue samples.

2. Use of Partial HKID-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the HKID-1 sequences or portions thereof, e.g., fragments derived from the noncoding regions of SEQ ID NO:1 having a length of at least 20 or 30 bases.

The HKID-1 sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such HKID-1 probes can be used to identify tissue by species and/or by organ type.

In a similar fashion, these reagents, e.g., HKID-1 primers or probes can be used to screen tissue culture for contamination (i.e., screen for the presence of a mixture of different types of cells in a culture).

C. Predictive Medicine

The present invention also provides the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining HKID-1 protein and/or nucleic acid expression as well as HKID-1 activity, in the context of a biological sample (e.g., blood, serum, cells, tissue) to thereby determine whether an individual is afflicted with a disease or disorder, or is at risk of developing a disorder, associated with aberrant HKID-1 expression or activity. The invention also provides for prognostic (or predictive) assays for determining whether an individual is at risk of developing a disorder associated with HKID-1 protein, nucleic acid expression or activity. For example, mutations in an HKID-1 gene can be assayed in a biological sample. Such assays can be used for prognostic or predictive purpose to thereby prophylactically treat an individual prior to the onset of a disorder characterized by or associated with HKID-1 protein, nucleic acid expression or activity.

Another aspect of the invention provides methods for determining HKID-1 protein, nucleic acid expression or HKID-1 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention provides monitoring the influence of agents (e.g., drugs or other compounds) on the expression or activity of HKID-1 in clinical trials.

These and other agents are described in further detail in the following sections.

1. Diagnostic Assays

An exemplary method for detecting the presence or absence of HKID-1 in a biological sample involves obtaining a biological sample from a test subject and contacting the biological sample with a compound or an agent capable of detecting HKID-1 protein or nucleic acid (e.g., mRNA, genomic DNA) that encodes HKID-1 protein such that the presence of HKID-1 is detected in the biological sample. An agent for detecting HKID-1 mRNA or genomic DNA can be a labeled nucleic acid probe capable of hybridizing to HKID-1 mRNA or genomic DNA. The nucleic acid probe can be, for example, a full-length HKID-1 nucleic acid, such as the nucleic acid of SEQ ID NO:1 or 3, or a portion thereof, such as an oligonucleotide of at least 15, 30, 50, 100, 250 or 500 nucleotides in length and sufficient to specifically hybridize under stringent conditions to HKID-1 mRNA or genomic DNA. Other suitable probes for use in the diagnostic assays of the invention are described herein.

An agent for detecting HKID-1 protein can be an antibody capable of binding to HKID-1 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect HKID-1 mRNA, protein, or genomic DNA in a biological sample in vitro as well as in vivo. For example, in vitro techniques for detection of HKID-1 mRNA include Northern hybridizations and in situ hybridizations. In vitro techniques for detection of HKID-1 protein include enzyme linked immunosorbent assays (ELISAs), Western blots, immunoprecipitations and immunofluorescence. In vitro techniques for detection of HKID-1 genomic DNA include Southern hybridizations. Furthermore, in vivo techniques for detection of HKID-1 protein include introducing into a subject a labeled anti-HKID-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A biological sample is a peripheral blood leukocyte sample isolated by conventional means from a subject.

In another embodiment, the methods further involve obtaining a control biological sample from a control subject, contacting the control sample with a compound or agent capable of detecting HKID-1 protein, mRNA, or genomic DNA, such that the presence of HKID-1 protein, mRNA or genomic DNA is detected in the biological sample, and comparing the presence of HKID-1 protein, mRNA or genomic DNA in the control sample with the presence of HKID-1 protein, mRNA or genomic DNA in the test sample.

The invention also encompasses kits for detecting the presence of HKID-1 in a biological sample (a test sample). Such kits can be used to determine if a subject is suffering from or is at increased risk of developing a disorder associated with aberrant expression of HKID-1 (e.g., an immunological disorder). For example, the kit can comprise a labeled compound or agent capable of detecting HKID-1 protein or mRNA in a biological sample and means for determining the amount of HKID-1 in the sample (e.g., an anti-HKID-1 antibody or an oligonucleotide probe which binds to DNA encoding HKID-1, e.g., SEQ ID NO:1 or SEQ ID NO:3). Kits can also include instructions for observing that the tested subject is suffering from or is at risk of developing a disorder associated with aberrant expression of HKID-1 if the amount of HKID-1 protein or mRNA is above or below a normal level.

For antibody-based kits, the kit can comprise, for example: (1) a first antibody (e.g., attached to a solid support) which binds to HKID-1 protein; and, optionally, (2) a second, different antibody which binds to HKID-1 protein or the first antibody and is conjugated to a detectable agent.

For oligonucleotide-based kits, the kit can comprise, for example: (1) an oligonucleotide, e.g., a detectably labeled oligonucleotide, which hybridizes to an HKID-1 nucleic acid sequence or (2) a pair of primers useful for amplifying an HKID-1 nucleic acid molecule;

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of HKID-1.

2. Prognostic Assays

The methods described herein can furthermore be utilized as diagnostic or prognostic assays to identify subjects having or at risk of developing a disease or disorder associated with aberrant HKID-1 expression or activity. For example, the assays described herein, such as the preceding diagnostic assays or the following assays, can be utilized to identify a subject having or at risk of developing a disorder associated with HKID-1 protein, nucleic acid expression or activity.

Alternatively, the prognostic assays can be utilized to identify a subject having or at risk for developing such a disease or disorder. Thus, the present invention provides a method in which a test sample is obtained from a subject and HKID-1 protein or nucleic acid (e.g., mRNA, genomic DNA) is detected, wherein the presence of HKID-1 protein or nucleic acid is diagnostic for a subject having or at risk of developing a disease or disorder associated with aberrant HKID-1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant HKID-1 expression or activity. For example, such methods can be used to determine whether a subject can be effectively treated with a specific agent or class of agents (e.g., agents of a type which decrease HKID-1 activity). Thus, the present invention provides methods for determining whether a subject can be effectively treated with an agent for a disorder associated with aberrant HKID-1 expression or activity in which a test sample is obtained and HKID-1 protein or nucleic acid is detected (e.g., wherein the presence of HKID-1 protein or nucleic acid is diagnostic for a subject that can be administered the agent to treat a disorder associated with aberrant HKID-1 expression or activity).

The methods of the invention can also be used to detect genetic lesions or mutations in an HKID-1 gene, thereby determining if a subject with the lesioned gene is at risk for a disorder characterized by aberrant cell proliferation and/or differentiation. In embodiments, the methods include detecting, in a sample of cells from the subject, the presence or absence of a genetic lesion or mutation characterized by at least one of an alteration affecting the integrity of a gene encoding an HKID-1-protein, or the mis-expression of the HKID-1 gene. For example, such genetic lesions or mutations can be detected by ascertaining the existence of at least one of: 1) a deletion of one or more nucleotides from an HKID-1 gene; 2) an addition of one or more nucleotides to an HKID-1 gene; 3) a substitution of one or more nucleotides of an HKID-1 gene; 4) a chromosomal rearrangement of an HKID-1 gene; 5) an alteration in the level of a messenger RNA transcript of an HKID-1 gene; 6) an aberrant modification of an HKID-1 gene, such as of the methylation pattern of the genomic DNA; 7) the presence of a non-wild type splicing pattern of a messenger RNA transcript of an HKID-1 gene; 8) a non-wild type level of an HKID- 1-protein; 9) an allelic loss of an HKID-1 gene; and 10) an inappropriate post-translational modification of an HKID-1-protein. As described herein, there are a large number of assay techniques known in the art which can be used for detecting lesions in an HKID-1 gene. A biological sample is a peripheral blood leukocyte sample isolated by conventional means from a subject.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the HKID-1-gene (see, e.g., Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to an HKID-1 gene under conditions such that hybridization and amplification of the HKID-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an HKID-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g. U.S. Pat. No. 5,498,531) can be used to score for the presence of specific mutations by development or loss of a ribozyme cleavage site.

In other embodiments, genetic mutations in HKID-1 can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations in HKID-1 can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the HKID-1 gene and detect mutations by comparing the sequence of the sample HKID-1 with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the HKID-1 gene include methods in which protection from cleavage agents is used to detect mismatched bases in RNA/RNA or RNA/DNA heteroduplexes (Myers et al. (1985) *Science* 230:1242). In general, the technique of "mismatch cleavage" entails providing heteroduplexes formed by hybridizing (labeled) RNA or DNA containing the wild-type HKID-1 sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S1 nuclease to digest mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in HKID-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on an HKID-1 sequence, e.g., a wild-type HKID-1 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in HKID-1 genes. For example, single strand conformation polymorphism (SSCP) may be used to detect differences in electrophoretic mobility between mutant and wild type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). Single-stranded DNA fragments of sample and control HKID-1 nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In an embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent or reduce polymerase extension (Prossner (i1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (3arany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an HKID-1 gene.

Furthermore, any cell type or tissue, preferably peripheral blood leukocytes, in which HKID-1 is expressed may be utilized in the prognostic assays described herein.

3. Pharmacogenomics

Agents, or modulators which have a stimulatory or inhibitory effect on HKID-1 activity (e.g., HKID-1 gene expression) as identified by a screening assay described herein can be administered to individuals to treat (prophylactically or therapeutically) disorders (e.g., disorders involving cells or tissues in which HKID-1 is expressed, such as cells of the nervous system) associated with aberrant HKID-1 activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of HKID-1 protein, expression of HKID-1 nucleic acid, or mutation content of HKID-1 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of HKID-1 protein, expression of HKID-1 nucleic acid, or mutation content of HKID-1 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an HKID-1 modulator, such as a modulator identified by one of the exemplary screening assays described herein.

4. Monitoring of Effects During Clinical Trials

Monitoring the influence of agents (e.g., drugs, compounds) on the expression or activity of HKID-1 (e.g., the ability to modulate aberrant cell proliferation and/or differentiation) can be applied not only in basic drug screening, but also in clinical trials. For example, the effectiveness of an agent, as determined by a screening assay as described herein, to increase HKID-1 gene expression, protein levels or protein activity, can be monitored in clinical trials of subjects exhibiting decreased HKID-1 gene expression, protein levels, or protein activity. Alternatively, the effectiveness of an agent, as determined by a screening assay, to decrease HKID-1 gene expression, protein levels or protein activity, can be monitored in clinical trials of subjects exhibiting increased HKID-1 gene expression, protein levels, or protein activity. In such clinical trials, HKID-1 expression or activity and preferably, that of other genes that have been implicated in for example, a cellular proliferation disorder, can be used as a marker of the immune responsiveness of a particular cell.

For example, and not by way of limitation, genes, including HKID-1, that are modulated in cells by treatment with an agent (e.g., compound, drug or small molecule) which modulates HKID-1 activity (e.g., as identified in a screening assay described herein) can be identified. Thus, to study the effect of agents on cellular proliferation disorders, for example, in a clinical trial, cells can be isolated and RNA prepared and analyzed for the levels of expression of HKID-1 and other genes implicated in the disorder. The levels of gene expression (i.e., a gene expression pattern) can be quantified by Northern blot analysis or RT-PCR, as described herein, by hybridization to a multiple tissue expression array as described in Example 2, or alternatively by measuring the amount of protein produced, by one of the methods as described herein, or by measuring the levels of activity of HKID-1 or other genes. In this way, the gene expression pattern can serve as a marker, indicative of the physiological response of the cells to the agent. Accordingly, this response state may be determined before, and at various points during, treatment of the individual with the agent.

In an embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of an HKID-1 protein, mRNA, or genomic DNA in the preadministration sample; (iii) obtaining one or more post-administration samples from the subject; (iv) detecting the level of expression or activity of the HKID-1 protein, mRNA, or genomic DNA in the post-administration samples; (v) comparing the level of expression or activity of the HKID-1 protein, mRNA, or genomic DNA in the pre-administration sample with the HKID-1 protein, mRNA, or genomic DNA in the post administration sample or samples; and (vi) altering the administration of the agent to the subject accordingly. For example, increased administration of the agent may be desirable to increase the expression or activity of HKID-1 to higher levels than detected, i.e., to increase the effectiveness of the agent. Alternatively, decreased administration of the agent may be desirable to decrease expression or activity of HKID-1 to lower levels than detected, i.e., to decrease the effectiveness of the agent.

D. Methods of Treatment

The present invention provides for both prophylactic and therapeutic methods of treating a subject at risk of (or susceptible to) a disorder or having a disorder associated with aberrant HKID-1 expression or activity.

1. Prophylactic Methods

In one aspect, the invention provides a method for preventing in a subject, a disease or condition associated with an aberrant HKID-1 expression or activity, by administering to the subject an agent which modulates HKID-1 expression or at least one HKID-1 activity. Subjects at risk for a disease which is caused or contributed to by aberrant HKID-1 expression or activity can be identified by, for example, any or a combination of diagnostic or prognostic assays as described herein. Administration of a prophylactic agent can occur prior to the manifestation of symptoms characteristic of the HKID-1 aberrancy, such that a disease or disorder is prevented or, alternatively, delayed in its progression. Depending on the type of HKID-1 aberrancy, for example, an HKID-1 agonist or HKID-1 antagonist agent can be used for treating the subject. The appropriate agent can be determined based on screening assays described herein.

2. Therapeutic Methods

Another aspect of the invention provides methods of modulating HKID-1 expression or activity for therapeutic purposes. The modulatory method of the invention involves contacting a cell with an agent that modulates one or more of the activities of HKID-1 protein activity associated with the cell. An agent that modulates HKID-1 protein activity can be an agent as described herein, such as a small molecule, e.g., a small molecule that modulates the protein kinase activity of HKID-1, a nucleic acid or a protein, a naturally-occurring cognate ligand of an HKID-1 protein, a peptide, or an HKID-1 peptidomimetic. In one embodiment, the agent stimulates one or more of the biological activities of HKID-1 protein. Examples of such stimulatory agents include small molecules that stimulate one or more activities of HKID-1, e.g., the HKID-1 protein kinase activity, active HKID-1 protein and a nucleic acid molecule encoding HKID-1 that has been introduced into the cell. In another embodiment, the agent inhibits one or more of the biological activities of HKID-1 protein. Examples of such inhibitory agents include a small molecule that inhibits one or more HKID-1 activity, e.g., HKID-1 protein kinase activity, anti-sense HKID-1 nucleic acid molecules and anti-HKID-1 antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of an HKID-1 protein or nucleic acid molecule. The present invention also provides methods of treating an individual afflicted with a disease or disorder that can be treated by modulating the activity of HKID-1 an HKID-1 protein or nucleic acid molecule. In one embodiment, the method involves administering an agent, e.g., a small molecule, (e.g., an agent identified by a screening assay described herein), or combination of agents that modulates (e.g., upregulates or downregulates) HKID-1 expression or activity.

Stimulation of HKID-1 activity is desirable in situations in which HKID-1 is abnormally downregulated and/or in which increased HKID-1 activity is likely to have a beneficial effect. Conversely, inhibition of HKID-1 activity is desirable in situations in which HKID-1 is abnormally upregulated and/or in which decreased HKID-1 activity is likely to have a beneficial effect.

This invention is further illustrated by the following examples which should not be construed as limiting. The contents of all references, patents and published patent applications cited throughout this application are hereby incorporated by reference.

EXAMPLES

Example 1

Determination of the Nucleotide Sequence of HKID-1

Human HKID-1 cDNAs isolated from cDNA libraries constructed in standard cloning vectors were sequenced. The cDNA sequences were assembled into a contig and the HKID-1 sequence was determined from the consensus sequence of this contig. Analysis of the contig revealed an approximately 2126 kb HKID-1 cDNA sequence with a 978 base pair open reading frame predicted to encode a novel 326 amino acid protein.

Example 2

Distribution of HKID-1 mRNA in Human Tissues

HKID-1 mRNA expression was analyzed by hybridizing a radioactively labeled HKID-1-specific DNA probe to human poly A+ RNA arrayed on a nylon membrane (the Human Multiple Tissue Expression (MTE) Array, Clontech; Palo Alto, Calif.). Poly A+ RNAs from the following human tissues and cell lines are present on the MTE Array, whole brain, cerebral cortex, frontal lobe, parietal lobe, occipital lobe, temporal lobe, paracentral gyrus of cerebral cortex, pons, left cerebellum, right cerebellum, corpus callosum, amygdala, caudate nucleus, hippocampus, medulla oblongata, putamen, substantia nigra, accumbens nucleus, thalamus, pituitary gland, spinal cord, heart, aorta, left atrium, right atrium, left ventricle, right ventricle, interventricular septum, apex of the heart, esophagus, stomach, duodenum, jejunum, ileum, ilocecum, appendix, ascending colon, transverse colon, descending colon, rectum, kidney, skeletal muscle, spleen, thymus, peripheral blood leukocyte, lymph node, bone marrow, trachea, lung, placenta, bladder, uterus, prostate, testis, ovary, liver, pancreas, adrenal gland, thyroid gland, salivary gland, mammary gland, HL-60 leukemia cell line, S3 HeLa cell line, K-562 leukemia cell line, MOLT-4 leukemia cell line, Raji Burkitt's lymphoma cell line, Daudi Burkitt's lymphoma cell line, SW480 colorectal adeno-carcinoma cell line, A549 lung carcinoma cell line, fetal brain, fetal heart, fetal kidney, fetal liver, fetal spleen, fetal thymus, fetal lung.

In more detail, a portion of the HKID-1 cDNA was synthesized using PCR for use as a hybridization probe. The HKID-1 specific DNA was radioactively labeled with 32P-dCTP using the Prime-It kit (Stratagene; La Jolla, Calif.) according to the instructions of the supplier. The MTE array filter was probed with the radiolabeled HKID-1 specific DNA probe in ExpressHyb hybridization solution (Clontech) and washed at high stringency according to the manufacturer's recommendations. These studies revealed that HKID-1 mRNA is expressed in all tissues contained in the MTE array. The highest expression in adult tissues was detected in placenta then trachea then lung then peripheral blood leukocytes then heart. In fetal tissues, the highest expression was detected in lung then heart then kidney then spleen. Low expression of HKID-1 mRNA was detected in all tissues analyzed. HKID-1 mRNA expression was weak overall in both adult and fetal brain except in adult substantia nigra and adult pituitary gland in which HKID-1 mRNA levels were moderate.

Example 3

Characterization of HKID-1 Protein

In this example, the predicted amino acid sequence of human HKID-1 protein was compared to amino acid sequences of known motifs and/or domains present in proteins and to the polypeptide sequences of known proteins. Polypeptide domains and/or motifs present in HKID-1 were identified as were proteins with significant amino acid similarities to HKID-1. In addition, the molecular weight of the human HKID-1 protein was predicted.

The human HKID-1 nucleotide sequence (FIG. 1; SEQ ID NO:1), identified as described above, encodes a 326 amino acid protein (FIG. 1; SEQ ID NO:2). HKID-1 has a predicted MW of about 35.86 kDa, not including post-translational modifications. The HKID-1 polypeptide sequence of SEQ ID NO:2 was used to query the PROSITE database of protein patterns and to query a library of Hidden Markov Models (HMMs) which can recognize common protein domains and families. The search of the PROSITE database revealed the presence of one cAMP- and cGMP-dependent protein kinase phosphorylation site (PS00004; SEQ ID NO:4) from amino acids 260–263 of SEQ ID NO:2; SEQ ID NO:5; three protein kinase C phosphorylation sites (PS00005; SEQ ID NO:6) from amino acids 137–139, 275–277, and 279–281, of SEQ ID NO:2; SEQ ID NOS:7–9; three casein kinase II phosphorylation sites (PS00006; SEQ ID NO:10) from amino acids 202–205, 211–214, and 321–324, of SEQ ID NO:2; SEQ ID NOS:11–13; one tyrosine kinase phosphorylation site (PS00007; SEQ ID NO:14) from amino acid 33–40, of SEQ ID NO:2; SEQ ID NO:15; seven N-myristoylation sites (PS00008; SEQ ID NO:16) from amino acids 43–48, 49–54, 57–62, 63–68, 80–85, 98–103, and 295–300 of SEQ ID NO:2; SEQ ID NOS:17–23; one protein kinase ATP-binding region signature (PS00107; SEQ ID NO:24) from amino acid 46–54, of SEQ ID NO:2; SEQ ID NO:25; one serine/threonine protein kinase active site signature (PS00108; SEQ ID NO:26) from amino acid 166–178, of SEQ ID NO:2; SEQ ID NO:27. The search of the HMM database revealed the presence of one eukaryotic protein kinase domain (PF00069; SEQ ID NO:28) from amino acid 40–293, of SEQ ID NO:2; SEQ ID NO:29 with a score of 262.4 and E value of $5.9 \times 10^{-75}$ (see FIG. 2). For general information regarding PFAM identifiers, PS prefix and PF prefix motif identification numbers, refer to Sonnhammer et al. (1997) *Protein* 28:405–420 and http://www.psc.edu/general/software/packages/pfam/pfam.html.

The HKID-1 polypeptide sequence of SEQ ID NO:2 was used to query the PROTOT database of protein sequences using the BLASTP program with the BLOSUM62 matrix and a protein word length of 3. The five most closely related proteins to HKID-1 identified by this BLASTP analysis are listed: HKID-1 was found to be 95% identical over 326 amino acids to rat KID-1 (AF086624; SEQ ID NO:37) with a score of 1646, 77% identical to *Xenopus laevis* (frog) PIM-1 (Q91822; SEQ ID NO:38) with a score of 922, similar to murine PIM-1 (P06803; SEQ ID NO:39) with a score of 873, similar to rat PIM-1 (P26794; SEQ ID NO:40) with a score of 884, and similar to human PIM-1 (P11309; SEQ ID NO:41) with a score of 883.

FIG. 4 shows an alignment, carried out with the MegAlign program of the DNASTAR sequence analysis package using the J. Hein method with a PAM250 residue weight table, of the HKID-1 polypeptide sequence of SEQ ID NO:2 and the just listed five closest HKID-1 relatives identified by BLASTP analysis. Table 1 shows both the percent polypeptide sequence similarity and the percent polypeptide sequence divergence between HKID-1 and its five closest relatives identified by BLASTP analysis as well as the percent polypeptide sequence similarity and the percent polypeptide sequence divergence between said HKID-1 relatives and each other. Sequence pair distances were carried out with the MegAlign program of the DNASTAR sequence analysis package using the J. Hein method with a PAM250 residue weight table. These analyses indicate that HKID-1 is the species ortholog of rat KID-1 (Feldman, J. D. et al. (1998). J. Biol. Chem. 273:16535–16543) and frog PIM-1 because HKID-1 is more closely related to these two proteins than to PIM-1 proteins. It has been reported that frog PIM-1 and rat KID-1 are species orthologs (Feldman, J. D. et al. (1998). J. Biol. Chem. 273:16535–16543). HKID-1 is a paralog of human PIM-1, murine PIM-1, and rat PIM-1. HKID-1 plays some or all of the roles in human that its species orthologs, rat KID-1 and frog PIM-1, play in the species from which they originate.

The rat KID-1, frog PIM-1, and human and murine PIM-1 are all known to have serine/threonine protein kinase activity in in vitro phosphorylation assays. The high polypeptide sequence similarity between HKID-1 and rat KID-1, frog PIM-1, and human and murine PIM-1, HKID-1 demonstrates that HKID-1 is a serine/threonine protein kinase.

Rat KID-1 is described in Feldman, J. D. et al. (1998). J. Biol. Chem. 273:16535–16543. Rat KID-1 is induced in specific regions of the hippocampus and cortex in response to kainic acid and electroconvulsive shock suggesting that rat KID-1 is involved in neuronal function, synaptic plasticity, learning, and memory as well as kainic acid seizures and some nervous system-related diseases such as seizures and epilepsy. Because HKID-1 is the species ortholog of rat KID-1, HKID-1 is involved in some or all of the processes and diseases in which rat KID-1 is involved. In addition, the HKID-1 paralogs, the PIM-1 proteins, are proto-oncogenes. Consequently, it is possible that HKID-1 is involved in cell growth regulation, cancer, and related pathways and diseases.

TABLE 1

|  | frog PIM-1 | HKID-1 | human PIM-1 | murine PIM-1 | rat KID-1 | rat PIM-1 |  |
| --- | --- | --- | --- | --- | --- | --- | --- |
| frog PIM-1 | *** | 77.5 | 65.5 | 66.1 | 77.2 | 65.5 | frog PIM-1 |
| HKID-1 | 26.8 | *** | 68.7 | 68.4 | 95.4 | 69.0 | HKID-1 |
| human PIM-1 | 46.0 | 40.5 | *** | 93.9 | 68.7 | 97.1 | human PIM-1 |
| murine PIM-1 | 44.9 | 41.0 | 6.3 | *** | 68.4 | 94.3 | murine PIM-1 |
| rat KID-1 | 27.3 | 4.7 | 40.5 | 41.0 | *** | 68.7 | rat KID-1 |
| rat PIM-1 | 46.0 | 39.9 | 2.9 | 6.0 | 40.5 | *** | rat PIM-1 |

Table Legend: Pair distances of HKID-1 and the five most closely related proteins identified in a BLASTP analysis. Percent similarity is shown in the upper triangular quadrant and percent divergence in shown in the lower triangular quadrant. Sequence pair distances were carried out with the MegAlign program of the DNASTAR sequence analysis package using the J. Hein method with a PAM250 residue weight table.

Example 4

Preparation of HKID-1 Fusion Proteins

Recombinant HKID-1 can be produced in a variety of expression systems. For example, the mature HKID-1 peptide can be expressed as a recombinant glutathione-S-transferase (GST) fusion protein in *E. coli* and the fusion protein can be isolated and characterized. Specifically, as described above, HKID-1 can be fused to GST and this fusion protein can be expressed in *E. coli* strain PEB199. Expression of the GST-HKID-1 fusion protein in PEB 199 can be induced with IPTG. The recombinant fusion protein can be purified from crude bacterial lysates of the induced PEB199 strain by affinity chromatography on glutathione beads.

Example 5

Identification of the Chromosomal Location of HKID-1

To determine the chromosomal location of HKID-1, the HKID-1 nucleotide sequence of SEQ ID NO:1 was used to query, using the BLASTN program (Altschul S. F. et al, (1990) J. Mol. Biol. 215: 403–410.) with a word length of 12 and using the BLOSUM62 scoring matrix, a database of human nucleotide sequences originating from nucleotide molecules that have been mapped to the human genome. The WI-11798 nucleotide sequence was found to contain HKID-1 sequences establishing that WI-11798 and HKID-1 map to the same chromosomal location, chromosome 22 between the D22S1169 and D22S_qter markers, 196.70 centiRays from the top of the chromosome 22 linkage group.

Example 6

Tissue Distribution of HKID-1 mRNA by Large-Scale Tissue-Specific Library Sequencing Standard molecular biology methods (Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989) were used to construct cDNA libraries in plasmid vectors from multiple human tissues. Individual cDNA clones from each library were isolated and sequenced and their nucleotide sequences were input into a database. The HKID-1 nucleotide sequence of SEQ ID NO:1 was used to query the tissue-specific library cDNA clone nucleotide sequence database using the BLASTN program (Altschul S. F. et al, (1990) J. Mol. Biol. 215: 403–410.) with a word length of 12 and using the BLOSUM62 scoring matrix. Nucleotide sequences identical to portions of the HKID-1 nucleotide sequence of SEQ ID NO:1 were found in cDNA libraries originating from human skin, kidney, lung, heart, thymus, endothelial cells, prostate, uterus, lymph node, neuron, placenta, T-cell, breast and muscle. This result indicates that the HKID-1 mRNA, or fragments thereof, is expressed in the listed tissues, although it is not possible to draw any conclusion about the expression level of HKID-1 mRNA in said tissues. In addition, the fact that HKID-1-identical sequences were not detected in libraries originating from other tissues does not mean that the HKID-1 mRNA is not expressed in those tissues. HKID-1 nucleic acid sequences, fragments thereof, proteins encoded by these sequences, and fragments thereof as well as modulators of HKID-1 gene or protein activity may be useful for diagnosing or treating diseases that involve the tissues in which the HKID-1 mRNA is expressed.

Equivalents

Those skilled in the art will recognize, or be able to ascertain using no more than routine experimentation, many equivalents to the specific embodiments of the invention described herein. Such equivalents are intended to be encompassed by the following claims.

That which is claimed:

1. An isolated polypeptide comprising, the amino acid sequence of SEQ ID NO:2.

2. The polypeptide of claim 1, wherein said polypeptide is encoded by a nucleic acid molecule comprising the nucleotide sequence of SEQ ID NO:1 or SEQ ID NO:3.

3. The polypeptide of claim 1, further comprising heterologous amino acid sequences.

4. An isolated polypeptide which is the polypeptide set forth in SEQ ID NO:2.

5. The polypeptide of claim 4 further comprising heterologous amino acid sequences.

* * * * *

UNITED STATES PATENT AND TRADEMARK OFFICE
CERTIFICATE OF CORRECTION

PATENT NO. : 6,383,791 B1
DATED : May 7, 2002
INVENTOR(S) : Kapeller-Libermann

It is certified that error appears in the above-identified patent and that said Letters Patent is hereby corrected as shown below:

<u>Title page,</u>
Item [75], Inventor: "Rosanna Kapeller" should read
-- Rosanna Kapeller-Libermann --.

Signed and Sealed this

Twenty-ninth Day of October, 2002

Attest:

Attesting Officer

JAMES E. ROGAN
*Director of the United States Patent and Trademark Office*